(12) United States Patent
Weiser et al.

(10) Patent No.: US 10,883,026 B2
(45) Date of Patent: Jan. 5, 2021

(54) ADHESIVE BASED ON A SPECIAL POLYURETHANEUREA WITH ADJUSTABLE BONDING FORCE, AND PRODUCTION AND USE THEREOF

(71) Applicant: Covestro Deutschland AG, Leverkusen (DE)

(72) Inventors: Marc-Stephan Weiser, Kürten-Dürscheid (DE); Sascha Plug, Leverkusen (DE); Sebastian Doerr, Düsseldorf (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/764,466

(22) PCT Filed: Dec. 13, 2018

(86) PCT No.: PCT/EP2018/084672
§ 371 (c)(1),
(2) Date: May 15, 2020

(87) PCT Pub. No.: WO2019/121282
PCT Pub. Date: Jun. 27, 2019

(65) Prior Publication Data
US 2020/0354614 A1    Nov. 12, 2020

(30) Foreign Application Priority Data

Dec. 21, 2017    (EP) .................................... 17209627

(51) Int. Cl.
*A61L 15/00* (2006.01)
*A61L 24/00* (2006.01)
(Continued)

(52) U.S. Cl.
CPC .............. *C09J 175/08* (2013.01); *A61L 15/26* (2013.01); *A61L 15/58* (2013.01); *A61L 24/046* (2013.01);
(Continued)

(58) Field of Classification Search
CPC .......... A61L 15/00; A61L 15/20; A61L 15/26; A61L 15/50; A61L 15/58; A61L 24/00;
(Continued)

(56) References Cited

U.S. PATENT DOCUMENTS

| 4,404,296 A | 9/1983 | Schapel |
| 4,661,099 A | 4/1987 | von Bittera et al. |

(Continued)

FOREIGN PATENT DOCUMENTS

| DE | 102007052966 A | 5/2009 |

OTHER PUBLICATIONS

International Search Report PCT/EP2018/084672, dated Mar. 20, 2019, Authorized officer: Martin Sütterlin.
(Continued)

*Primary Examiner* — Jacob T Minskey
*Assistant Examiner* — Matthew Hoover
(74) *Attorney, Agent, or Firm* — Jed C. Benson

(57) ABSTRACT

The present invention relates to an adhesive producible from an aqueous polyurethaneurea dispersion comprising an amorphous polyurethaneurea (V1) obtainable by reacting at least A) one aliphatic, cycloaliphatic or araliphatic polyisocyanate component having an average isocyanate functionality of ≥1.8 and ≤2.6, B) one polyetherpolyol component, C) one amino-functional chain extender component having at least 2 isocyanate-reactive amino groups, containing at least one amino-functional compound C1) that does not have any ionic or ionogenic groups and/or an amino-functional compound C2) that has ionic or ionogenic groups, D) optionally further hydrophilizing components different than C2), E) optionally hydroxy-functional compounds having a molecular weight of 62 to 399 mol/g, F) optionally further polymeric polyols that are different than B), G) optionally one compound having exactly one isocyanate-reactive group or one compound having more than one isocyanate-reactive group, where only one of the isocyanate-reactive groups reacts with the isocyanate groups present in the reaction mixture under the reaction conditions chosen, and H) optionally one aliphatic, cycloaliphatic or araliphatic polyisocyanate component having an average isocyanate functionality of >2.6 and ≤4, where components B) and F) together contain ≤30% by weight of component F), based on the total mass of components B) and F) and a hydrophilic polyisocyanate (V2) preparable at least from the components of I) an aliphatic, cycloaliphatic or araliphatic polyisocyanate component having an average isocyanate functionality of preferably ≥2.0 and ≤3.6, J) a polymeric, hydrophilic and monofunctional polyalkylene oxide component, K) optionally further hydrophilizing components different than J), L) optionally admixtures and auxiliaries.

The invention likewise provides an adhesive layer and a product including the adhesive, a process for producing the adhesive layer, a specific polyurethaneurea, and the use of the adhesive and a kit having components (V1) and (V2).

15 Claims, No Drawings

(51) Int. Cl.

| | | |
|---|---|---|
| *A61L 26/00* | (2006.01) | |
| *C08G 18/00* | (2006.01) | |
| *C09J 175/00* | (2006.01) | |
| *C09J 175/08* | (2006.01) | |
| *A61L 15/26* | (2006.01) | |
| *C08G 18/73* | (2006.01) | |
| *C08G 18/75* | (2006.01) | |
| *C08G 18/12* | (2006.01) | |
| *C08G 18/32* | (2006.01) | |
| *C08G 18/08* | (2006.01) | |
| *C08G 18/38* | (2006.01) | |
| *C08G 18/48* | (2006.01) | |
| *C08G 18/66* | (2006.01) | |
| *A61L 24/04* | (2006.01) | |
| *A61L 15/58* | (2006.01) | |

(52) U.S. Cl.
CPC ...... *A61L 26/0019* (2013.01); *C08G 18/0828* (2013.01); *C08G 18/0866* (2013.01); *C08G 18/12* (2013.01); *C08G 18/3228* (2013.01); *C08G 18/3275* (2013.01); *C08G 18/3857* (2013.01); *C08G 18/4808* (2013.01); *C08G 18/4825* (2013.01); *C08G 18/6688* (2013.01); *C08G 18/73* (2013.01); *C08G 18/755* (2013.01)

(58) Field of Classification Search
CPC ........ A61L 24/04; A61L 24/046; A61L 26/00; A61L 26/001; A61L 26/0019; C08G 18/00; C08G 18/08; C08G 18/082; C08G 18/0828; C08G 18/086; C08G 18/0866; C08G 18/10; C08G 18/12; C08G 18/30; C08G 18/32; C08G 18/322; C08G 18/3228; C08G 18/327; C08G 18/3275; C08G 18/38; C08G 18/385; C08G 18/3857; C08G 18/40; C08G 18/48; C08G 18/48; C08G 18/4808; C08G 18/482; C08G 18/4825; C08G 18/60; C08G 18/66; C08G 18/668; C08G 18/6688; C08G 18/70; C08G 18/73; C08G 18/75; C08G 18/755; C09J 175/00; C09J 175/08

See application file for complete search history.

(56) References Cited

U.S. PATENT DOCUMENTS

| | | | | |
|---|---|---|---|---|
| 6,191,216 | B1* | 2/2001 | Ganster | ............... C08G 18/227 523/111 |
| 6,642,304 | B1* | 11/2003 | Hansen | ................. C08G 18/12 428/423.1 |
| 2019/0233691 | A1* | 8/2019 | Dorr | ..................... C08G 18/10 |

OTHER PUBLICATIONS

Ullmanns Encyclopädie der technischen Chemie [Ullmann's Encyclopedia of Industrial Chemistry], 4th edition, vol. 19, Verlag Chemie, Weinheim p. 31-38.

* cited by examiner

* # ADHESIVE BASED ON A SPECIAL POLYURETHANEUREA WITH ADJUSTABLE BONDING FORCE, AND PRODUCTION AND USE THEREOF

CROSS-REFERENCE TO RELATED APPLICATION

This application is a national stage application under 35 U.S.C. § 371 of PCT/EP2018/084672, filed Dec. 13, 2018, which claims the benefit of European Application No. 17209627, filed Dec. 21, 2017, each of which is incorporated herein by reference.

FIELD

The present invention relates to a, preferably amorphous adhesive producible from an aqueous polyurethaneurea dispersion containing a specific, preferably amorphous polyurethaneurea with adjustable bonding force, and to an adhesive layer and to a product containing the adhesive. The invention likewise provides an aqueous dispersion containing the specific, preferably amorphous polyurethaneurea and for the possible uses thereof. This preferably amorphous adhesive can be produced in a very efficient manner.

BACKGROUND

In many applications, especially medical applications, for example self-adhesive bandages, plasters or other means of wound coverage, self-adhesive materials are used. The demands on self-adhesive materials may be very varied. What is common to the self-adhesive materials is that the adhesive has good adhesion on the surface to be fixed, but can at the same time be readily removed again, as far as possible without residues. In medical use, it is very advantageous to provide an adhesive for fixing of a wide variety of different articles, such as plasters, bandages, tapes or other means of wound coverage, which on the one hand stick well over a long period of time, for example several days or weeks, but after the wearing time are removable again without damage to the upper skin layers and preferably without pain. Furthermore, the adhesive should not leave any residues on the skin after it has been removed, should not trigger any allergies in order to avoid skin irritation, should be breathable and at the same time stable to water, and have good adhesion on the carrier material of the adhesive (e.g. film).

Self-adhesive acrylate or silicone adhesives are often used in such products. While acrylate adhesives also enable high bond strengths, as a result of their thermoplastic flow characteristics on the skin, they are typically removable again after a prolonged wearing time only with damage to the uppermost skin layers and with great pain; they lead to severe skin irritation and possibly to allergic reactions. Silicone adhesives, by contrast, frequently have a lower bonding force and therefore do not enable sufficiently high bond force for reliable bonding, especially over a long period, for various medical applications such as NPWT (negative pressure wound therapy), ostomy (artificial anus) and various medical adhesive tapes, for example surgical tapes.

In general, it is necessary to find a good balance of sufficient bonding force for a sufficiently long wearing time and gentle detachment of the adhesive on removal of the dressing from the skin. This is different from application to application. However, adhesives based on unpublished European patent application EP16177199.3 do not allow an adjustable bonding force. For bonding to wounds, sensitive or fragile skin, the adhesives from EP16177199.3 are not very suitable as a result of their high bond strength and the buildup of bonding force over time. By contrast, existing adhesives on the market, such as the systems described in EP897406, EP147588 and EP57839 are producible only by a complicated two-component mixing process, which, for typical adhesives manufacturers, is a complex procedure controllable only with difficulty.

SUMMARY

It is an object of the present invention to at least partly improve upon at least some of the disadvantages of the prior art.

It is a further object of the present invention to provide a skin-friendly pressure-sensitive adhesive for medical use having a sufficiently high bond force, especially to define within a range from 0.3 N/20 mm to 25 N/20 mm against aluminum to DIN EN 1464 (90° roller peel test) on a tensile tester according to DIN EN ISO 527-1.

It is a further object of the invention to provide an adhesive, for example in the form of an adhesive layer, that permits a simple and cost-effective mode of production.

It is additionally an object of the invention to provide an adhesive that allows very simple processibility, i.e. has a maximum "pot life", such that it is possible directly at the site of production, preferably from a single vessel, preferably for several hours, to work with the complete mixture of all components of the formulation.

In addition, it is an object of the invention to provide an adhesive, for example in the form of an adhesive layer, that has good skin compatibility, coupled with high wear comfort and good removability. More particularly, wear comfort and residue-free removability should be assured even after a wearing time of several weeks, especially on wounds and on fragile or sensitive skin.

It is another object of the invention to provide an adhesive, for example in the form of an adhesive layer, that has a high bonding force combined with good skin compatibility and very good removability, especially on wounds and on fragile or sensitive skin.

It is a further object of the invention to provide an adhesive, for example in the form of an adhesive layer that has the same advantages as described for the adhesive and is usable in various medical applications, but also industrial applications, for example both in the professional woundcare sector and in the OTC woundcare sector.

In addition, it is an object of the invention to provide an aqueous polyurethaneurea dispersion from which the adhesive or adhesive layer according to the invention can be obtained in a simple manner.

It is an additional object of the invention to provide a process for producing an adhesive layer which contains the polyurethaneurea dispersion of the invention and has all the advantages of the adhesive layer of the invention.

It is an object of the invention to provide for use of the adhesive or adhesive layer for securing of articles, preferably on the skin, wherein the adhesive or adhesive layer introduces the advantages already mentioned into the article or securing means.

It is a further object of the invention to provide for the use of a polyurethaneurea dispersion for production of an adhesive, an adhesive layer or a product that has the advantages already mentioned.

At least one of the objects is achieved by an adhesive according to the subject matter of claim 1. Particular embodiments are described in the dependent claims. In addition, at least some of the objects are achieved by an adhesive layer or a product including the adhesive of the invention. Some of the objects again are achieved by the execution of the process for producing the adhesive layer.

DETAILED DESCRIPTION

The invention firstly provides an adhesive producible from an aqueous polyurethaneurea dispersion comprising
(V1) a preferably amorphous polyurethaneurea (V1) obtainable by reacting at least
A) one aliphatic, cycloaliphatic or araliphatic polyisocyanate component having an average isocyanate functionality of ≥1.8 and ≤2.6,
B) one polymeric polyetherpolyol component,
C) one amino-functional chain extender component having at least 2 isocyanate-reactive amino groups, containing at least one amino-functional compound C1) that does not have any ionic or ionogenic groups and/or an amino-functional compound C2) that has ionic or ionogenic groups,
D) optionally further hydrophilizing components different than C2),
E) optionally hydroxy-functional compounds having a molecular weight of 62 to 399 mol/g,
F) optionally further polymeric polyols that are different than B),
G) optionally one compound having exactly one isocyanate-reactive group or one compound having more than one isocyanate-reactive group, where only one of the isocyanate-reactive groups reacts with isocyanate groups present in the reaction mixture under the reaction conditions chosen, and
H) optionally one aliphatic, cycloaliphatic or araliphatic polyisocyanate component having an average isocyanate functionality of >2.6 and ≤4, where components B) and F) together contain ≤30% by weight of component F), based on the total mass of components B) and F), and
(V2) a hydrophilic polyisocyanate preparable at least from the components of
I) an aliphatic, cycloaliphatic or araliphatic polyisocyanate component having an average isocyanate functionality of preferably ≥2.0 and ≤3.6,
J) a polymeric, hydrophilic and monofunctional polyalkylene oxide component,
K) optionally further, preferably hydrophilizing components different than J),
L) optionally admixtures and auxiliaries.

Preferably, the adhesive has a ratio of the polyurethaneurea (V1) to the polyisocyanate (V2) within a range from 80:1 to 1.2:1 or preferably within a range from 60:1 to 2:1, or preferably within a range from 40:1 to 4:1.

The adhesive is preferably amorphous. In the context of this invention, "amorphous" means that the polyurethaneurea, within the temperature range specified in the test method adduced hereinafter, forms only such small crystalline components, if any, that only one or more glass transition points $T_g$ but no melting regions having an enthalpy of fusion of ≥20 J/g can be found within the temperature range specified by means of the DSC measurements described.

Preferably, the aqueous polyurethaneurea dispersion has a ratio of the polyurethaneurea (V1) to the diisocyanate (V2) within a range from 200:1 to 3:1 or preferably within a range from 150:1 to 15:1, or preferably within a range from 100:1 to 10:1.

Preferably amorphous polyurethaneureas in the context of the invention are polymeric compounds having at least two, preferably at least three, urethane-containing repeat units:

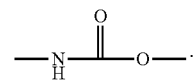

According to the invention, the preferably amorphous polyurethaneureas, by virtue of their preparation, also have repeat units that contain urea groups

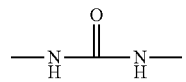

as formed particularly in the reaction of isocyanate-terminated prepolymers with amino-functional compounds.

Ionogenic groups in the context of this invention are understood to mean those functional groups that are capable of forming ionic groups, for example by neutralization with a base.

Component A) may be any polyisocyanate that the person skilled in the art would use for the purpose. Polyisocyanates suitable with preference as component A) are especially the aliphatic polyisocyanates known per se to the person skilled in the art that have an average isocyanate functionality of ≥1.8 and ≤2.6. The term "aliphatic" also includes cycloaliphatic and/or araliphatic polyisocyanates.

Mean isocyanate functionality is understood to mean the average number of isocyanate groups per molecule.

Preferred polyisocyanates are those in the molecular weight range from 140 to 336 g/mol. These are more preferably selected from the group consisting of 1,4-diisocyanatobutane (BDI), pentane 1,5-diisocyanate (PDI) 1,6-diisocyanatohexane (HDI), 1,3-bis(isocyanatomethyl)benzene (xylylene 1,3-diisocyanate, XDI), 1,4-bis(isocyanatomethyl)benzene (xylylene 1,4-diisocyanate, XDI), 1,3-bis(1-isocyanato-1-methyl-ethyl)benzene (TMXDI), 1,4-bis (1-isocyanato-1-methylethyl)benzene (TMXDI), 4-isocyanatomethyloctane 1,8-diisocyanate (trisisocyanatonononane (TIN)), 2-methyl-1,5-diisocyanatopentane, 1,5-diisocyanato-2,2-dimethylpentane, 2,2,4- or 2,4,4-trimethyl-1,6-diisocyanatohexane, 1,10-diisocyanatodecane, and the cycloaliphatic diisocyanates 1,3- or 1,4-diisocyanatocyclohexane, 1,4-diisocyanato-3,3,5-trimethylcyclohexane, 1,3-diisocyanato-2 (4)-methylcyclohexane, 1-isocyanato-3,3,5-trimethyl-5-isocyanatomethylcyclohexane (isophorone diisocyanate, IPDI), 1-isocyanato-1-methyl-4(3)isocyanatomethylcyclohexane, 1,8-diisocyanato-p-menthane, 4,4'-diisocyanato-1,1'-bi(cyclohexyl), 4,4'-diisocyanato-3,3'-dimethyl-1,1'-bi(cyclohexyl), 4,4'-diisocyanato-2,2',5,5'-tetramethyl-1,1'-bi(cyclohexyl), 4,4'- and/or 2,4'-diisocyanatodicyclohexylmethane, 4,4'-diisocyanato-3,3'-dimethyldicyclohexylmethane, 4,4'-diisocyanato-3,3',5,5'-tetramethyldicyclohexylmethane, 1,3-diisocyanatoadamantane, and 1,3-dimethyl-5,7-diisocyanatoadamantane or any mixtures of such isocyanates. The polyisocyanates are most preferably selected from butylene 1,4-diisocyanate, pentylene 1,5-diisocyanate (PDI), hexamethylene 1,6-diisocyanate (HDI), isophorone diisocyanate (IPDI), 2,2,4- and/or 2,4,4-trimethylhexamethylene diisocyanate, the isomeric bis(4,4'-isocyanatocyclohexyl)methanes or mixtures thereof with any isomer content (H12-MDI), cyclohexylene 1,4-diisocyanate, 4-isocyanatomethyloctane 1,8-diisocyanate (nonane triisocyanate) and alkyl 2,6-diisocyanatohexanoates (lysine diisocyanates) having C1-C8-alkyl groups.

As well as the aforementioned polyisocyanates, it is also possible to use modified diisocyanates having a mean isocyanate functionality ≥2 and ≤2.6, with uretdione, isocyanurate, urethane, allophanate, biuret, iminooxadiazinedione or oxadiazinetrione structure, and mixtures of proportions of these and/or the above.

Preference is given to polyisocyanates or polyisocyanate mixtures of the aforementioned type having exclusively aliphatically or cycloaliphatically bonded isocyanate groups or mixtures of these and a mean NCO functionality of the mixture of ≥1.8 and ≤2.6 and more preferably ≥2.0 and ≤2.4.

In a preferred embodiment of the adhesive, component A) contains an aliphatic or cycloaliphatic polyisocyanate selected from the group consisting of HDI, IPDI and/or H12-MDI or the modification products thereof, most preferably selected from HDI and/or IPDI.

In an especially preferred variant, IPDI and HDI are present in a mixture as component A).

The weight ratio of IPDI:HDI for the polyisocyanate component A) is preferably within a range from 1.05 to 10, more preferably within a range from 1.1 to 5, and most preferably within a range from 1.1 to 1.5.

In a preferred embodiment, the preferably amorphous polyurethaneurea used in accordance with the invention is prepared using ≥5% and ≤40% by weight of component A) and more preferably ≥10% and ≤35% by weight of component A), based in each case on the total mass of the preferably amorphous polyurethaneurea.

In a further preferred embodiment, the preferably amorphous polyurethaneurea is also prepared using component H), an aliphatic, cycloaliphatic or araliphatic polyisocyanate component having a mean isocyanate functionality (mean number of isocyanate groups per molecule) of >2.6 and ≤4, preferably ≥2.8 and ≤3.8. Component H) is preferably used in a mixture with component A).

Particularly suitable components H) are oligomeric diisocyanates having a functionality of >2.6 and ≤4, preferably ≥2.8 and ≤3.8, having isocyanurate, urethane, allophanate, biuret, iminooxadiazinedione or oxadiazinetrione structure. Most preferably, H) contains isocyanurate structures.

Preferably, the aliphatic, cycloaliphatic or araliphatic polyisocyanate component H) consists of an aliphatic or cycloaliphatic polyisocyanate oligomer based on HDI, IPDI and/or H12-MDI, most preferably based on HDI.

The molar ratio of the NCO groups from component A) to component H) is preferably 100:0.5 to 100:50, more preferably 100:2 to 100:15 and most preferably 100:3 to 100:8.

In a preferred embodiment, the preferably amorphous polyurethaneurea used in accordance with the invention is prepared using ≥0% and ≤10% by weight of component H) and more preferably ≥0.1% and ≤3% by weight of component H), based in each case on the total mass of the preferably amorphous polyurethaneurea.

The polymeric polyetherpolyols used in accordance with the invention as component B) preferably have number-average molecular weights within a range from 400 to 8000 g/mol, preferably within a range from 600 to 6000 g/mol, or preferably within a range from 1000 to 3000 g/mol, determined by gel permeation chromatography against polystyrene standard in tetrahydrofuran at 23° C., and/or an OH functionality of preferably within a range from 1.5 to 6, more preferably within a range from 1.8 to 3, more preferably within a range from 1.9 to 2.1. The expression "polymeric" polyetherpolyols here means more particularly that the polyols mentioned have at least two, preferably at least three, repeat units bonded to one another.

The number-average molecular weight is always determined in the context of this application by gel permeation chromatography (GPC) in tetrahydrofuran at 23° C. The procedure is according to DIN 55672-1: "Gel permeation chromatography, Part 1—Tetrahydrofuran as eluent" (SECurity GPC System from PSS Polymer Service, flow rate 1.0 ml/min; columns: 2×PSS SDV linear M, 8×300 mm, 5 μm; RID detector). Polystyrene samples of known molar mass are used for calibration. The number-average molecular weight is calculated with software support. Baseline points and evaluation limits are fixed according to DIN 55672 Part 1.

Suitable polyetherpolyols are, for example, the addition products, known per se, of styrene oxide, ethylene oxide, propylene oxide, butylene oxide and/or epichlorohydrin onto di- or polyfunctional starter molecules. Polyalkylene glycols in particular, such as polyethylene glycols, polypropylene glycols and/or polybutylene glycols, are applicable, especially with the abovementioned preferred molecular weights. Suitable starter molecules used may be all compounds known according to prior art, for example water, butyldiglycol, glycerol, diethylene glycol, trimethylolpropane, propylene glycol, sorbitol, ethylenediamine, triethanolamine, butane-1,4-diol.

In a preferred embodiment of the adhesive, component B) contains poly(propylene glycol) polyetherpolyols. Preferably, the adhesive includes poly(propylene glycol) polyetherpolyols within a range from 50% to 100% by weight, more preferably within a range from 70% to 100% by weight or preferably within a range from 90% to 100% by weight, more preferably to an extent of 100% by weight, based in each case on the total weight of component B).

If component B) has more than 50% by weight of poly (propylene glycol) polyetherpolyols, only a small amount of component G) is optionally used or, preferably, component G) is not used at all. If component B) for production of the adhesive should have more than 10% by weight, preferably more than 20% by weight, or preferably more than 30% by weight of poly(tetramethylene) polyetherpolyols, it is preferable that component G) is present.

In a preferred embodiment of the adhesive, component B) has an average molecular mass within a range from 400 to 4000 g/mol, or preferably within a range from 500 to 3500 g/mol, or preferably within a range from 800 to 3000 g/mol.

In a further preferred embodiment of the adhesive, component B) contains or consists of a mixture of poly(propylene glycol) polyetherpolyols having different average molecular weight, where the poly(propylene glycol) polyetherpolyols differ in their number-average molecular weights by at least 100 g/mol, preferably by at least 200 g/mol, or preferably by at least 400 g/mol, or preferably by at least 800 g/mol, or preferably by at least 1000 g/mol. Preferably, the number-average molecular weights of the poly(propylene glycol) polyetherpolyols differ by not more than 5000 g/mol, or by not more than 4000 g/mol, or by not more than 3000 g/mol.

In a particularly preferred embodiment, component B) contains a mixture of poly(propylene glycol) polyetherpolyols I having a number-average molecular weight $M_a$ of ≥400 and ≤1500 g/mol, more preferably of ≥600 and ≤1200 g/mol, most preferably of 1000 g/mol, and poly(propylene glycol)

polyetherpolyols II having a number-average molecular weight $M_n$ of ≥1500 and ≤8000 g/mol, more preferably of ≥1800 and ≤3000 g/mol, most preferably of 2000 g/mol.

The weight ratio of the poly(propylene glycol) polyetherpolyols I to the poly(propylene glycol) polyetherpolyols II is preferably in the range from 0.01 to 10, more preferably in the range from 0.02 to 5, most preferably in the range from 0.05 to 1.

According to the invention, the preferably amorphous polyurethaneurea is prepared using an amino-functional chain extender component C) having at least 2 isocyanate-reactive amino groups, containing at least one amino-functional compound C1) that does not have any ionic or ionogenic groups and/or an amino-functional compound C2) that has ionic or ionogenic groups.

The amino-functional compounds of component C) component are preferably selected from primary and/or secondary diamines. More particularly, the amino-functional compounds C) comprise at least one diamine.

In a preferred embodiment of the adhesive, the amino-functional component C) comprises at least one amino-functional compound C2) having ionic and/or ionogenic groups.

In a further preferred embodiment of the invention, the amino-functional component C) comprises both amino-functional compounds C2) having ionic and/or ionogenic groups and amino-functional compounds C1) having no ionic or ionogenic group.

For example, components C1) used may be organic di- or polyamines, for example ethylene-1,2-diamine, 1,2- and 1,3-diaminopropane, 1,4-diaminobutane, 1,6-diaminohexane, isophoronediamine (IPDA), isomer mixture of 2,2,4- and 2,4,4-trimethylhexamethylenediamine, 2-methylpentamethylenediamine, diethylenetriamine, 4,4-diaminodicyclohexylmethane and/or dimethylethylenediamine or mixtures of at least two of these.

Preferably, component C1) is selected from the group consisting of ethylene-1,2-diamine, bis(4-aminocyclohexyl)methane, 1,4-diaminobutane, IPDA, ethanolamine, diethanolamine and diethylenetriamine or a mixture of at least two of these.

In a further preferred embodiment, component C1) contains >75 mol %, more preferably ≥80 mol %, even more preferably ≥85 mol %, further preferably ≥95 mol % and still further preferably 100 mol % of ethylene-1,2-diamine or IPDA or a mixture of ethylene-1,2-diamine or IPDA, where the sum total of the two amines in relation to the total amount of C1) is preferably within the proportions mentioned.

Preferably, the hydrophilizing component C2) comprises at least one anionically hydrophilizing compound. Further preferably, the hydrophilizing component C2) includes an anionically hydrophilizing compound to an extent of at least 80% by weight, or preferably to an extent of at least 90% by weight, based on the total weight of components C2). More preferably, component C2) consists of exclusively anionically hydrophilizing compounds.

Suitable anionically hydrophilizing compounds contain at least one anionic or ionogenic group that can be converted to an anionic group. Further preferably, suitable anionically hydrophilizing compounds have at least two amino groups and more preferably two amino groups. More preferably, the hydrophilizing component C2) comprises or consists of an anionically hydrophilizing compound having at least one anionic or ionogenic group and at least two amino groups.

Suitable anionically hydrophilizing compounds as component C2), also called hydrophilizing agents C2) hereinafter, preferably contain a sulfonic acid or sulfonate group, more preferably a sodium sulfonate group. Suitable anionically hydrophilizing compounds as component C2) are especially the alkali metal salts of the mono- and diaminosulfonic acids. Examples of such anionic hydrophilizing agents are salts of 2-(2-aminoethylamino)ethanesulfonic acid, N-(propyl or butyl)ethylendiaminesulfonic acid or propylene-1,2- or -1,3-diamine-β-ethylsulfonic acid or mixtures of at least two of these.

Particularly preferred anionic hydrophilizing agents C2) are those that contain sulfonate groups as ionic groups and two amino groups, such as the salts of 2-(2-aminoethylamino)ethanesulfonic acid and propylene-1,3-diamine-β-ethylsulfonic acid. Very particular preference is given to using 2-(2-aminoethylamino)ethanesulfonic acid or salts thereof as anionic hydrophilizing agent C2).

The anionic group in component C2) may optionally also be a carboxylate or carboxylic acid group. In that case, component C2) is preferably selected from diaminocarboxylic acids. In this alternative embodiment, however, the carboxylic acid-based components C2) have to be used in higher concentrations compared to those components C2) bearing sulfonate or sulfonic acid groups. More preferably, therefore, the preferably amorphous polyurethaneurea is prepared using no hydrophilizing compounds bearing exclusively carboxylate groups as anionic groups of component C2).

In a preferred embodiment, the preferably amorphous polyurethaneurea used in accordance with the invention is prepared using ≥0.1% and ≤10% by weight of component C2) and more preferably ≥0.5% and ≤4% by weight of component C2), based in each case on the total mass of the preferably amorphous polyurethaneurea.

Hydrophilization can also be accomplished using mixtures of anionic hydrophilizing agents C2) and further hydrophilizing agents D) that are different than C2).

Suitable further hydrophilizing agents D) are, for example, nonionic hydrophilizing compounds D1) and/or hydroxy-functional ionic or ionogenic hydrophilizing agents D2). In a preferred embodiment of the adhesive, component D) comprises nonionically hydrophilizing components D1).

Suitable hydroxy-functional ionic or ionogenic hydrophilizing agents as component D2) are, for example, hydroxycarboxylic acids such as mono- and dihydroxycarboxylic acids, such as 2-hydroxyacetic acid, 3-hydroxypropanoic acid, 12-hydroxy-9-octadecanoic acid (ricinoleic acid), hydroxypivalic acid, lactic acid, dimethylolbutyric acid and/or dimethylolpropionic acid or mixtures of at least two of these. Preference is given to hydroxypivalic acid, lactic acid and/or dimethylolpropionic acid, particular preference to dimethylolpropionic acid. Preference is given to using no hydroxy-functional ionic or ionogenic hydrophilizing agents D2), especially preferably no hydrophilizing agents having carboxylate and hydroxyl groups, for example dimethylolpropionic acid. Preferably, the amount of hydroxy-functional ionic or ionogenic hydrophobizing agents D2) is present in the preferably amorphous polyurethaneurea within a range from 0% to 1% by weight, or preferably within a range from 0.01% 0.5% by weight, based on the total mass of the preferably amorphous polyurethaneurea.

Suitable nonionically hydrophilizing compounds as component D1) are, for example, polyoxyalkylene ethers having isocyanate-reactive groups, such as hydroxyl, amino or thiol groups. Preference is given to monohydroxy-functional polyalkylene oxide polyether alcohols having a statistical average of 5 to 70, preferably 7 to 55, ethylene oxide units per molecule, as obtainable in a manner known per se by alkoxylation of suitable starter molecules (for example in Ullmanns Encyclopadie der technischen Chemie [Ullmann's Encyclopedia of Industrial Chemistry], 4th edition, volume 19, Verlag Chemie, Weinheim p. 31-38). These are either pure polyethylene oxide ethers or mixed polyalkylene oxide ethers, where they contain at least 30 mol %, preferably at least 40 mol %, based on all alkylene oxide units present, of ethylene oxide units.

Particularly preferred nonionic compounds are monofunctional mixed polyalkylene oxide polyethers having 40 to 100 mol % of ethylene oxide units and 0 to 60 mol % of propylene oxide units.

Suitable starter molecules for such nonionic hydrophilizing agents are especially saturated monoalcohols such as methanol, ethanol, n-propanol, isopropanol, n-butanol, isobutanol, sec-butanol, the isomeric pentanols, hexanols, octanols and nonanols, n-decanol, n-dodecanol, n-tetradecanol, n-hexadecanol, n-octadecanol, cyclohexanol, the isomeric methylcyclohexanols or hydroxymethylcyclohexane, 3-ethyl-3-hydroxymethyloxetane or tetrahydrofurfuryl alcohol, diethylene glycol monoalkyl ethers, for example diethylene glycol monobutyl ether, unsaturated alcohols such as allyl alcohol, 1,1-dimethylallyl alcohol or olein alcohol, aromatic alcohols such as phenol, the isomeric cresols or methoxyphenols, araliphatic alcohols such as benzyl alcohol, anisyl alcohol or cinnamyl alcohol, secondary monoamines such as dimethylamine, diethylamine, dipropylamine, diisopropylamine, dibutylamine, bis(2-ethylhexyl) amine, N-methyl- and N-ethylcyclohexylamine or dicyclohexylamine, and heterocyclic secondary amines such as morpholine, pyrrolidine, piperidine or 1H-pyrazole. Preferred starter molecules are saturated monoalcohols of the aforementioned type. Particular preference is given to using diethylene glycol monobutyl ether, methanol or n-butanol as starter molecules.

Alkylene oxides suitable for the alkoxylation reaction are especially ethylene oxide and propylene oxide, which can be used in the alkoxylation reaction in any sequence or else in a mixture.

In a preferred embodiment of the invention, the preferably amorphous polyurethaneurea used in accordance with the invention contains ≥0% and ≤20% by weight of component D), preferably ≥0.1% and ≤10% by weight of component D) and most preferably ≥1% and ≤5% by weight of component D), based in each case on the total mass of the preferably amorphous polyurethaneurea. In a further preferred embodiment, component D) is not used for preparation of the preferably amorphous polyurethaneurea.

As component E) it is optionally possible to use polyols, especially nonpolymeric polyols, of said molecular weight range from 62 to 399 mol/g having up to 20 carbon atoms, such as ethylene glycol, diethylene glycol, triethylene glycol, propane-1,2-diol, propane-1,3-diol, butane-1,4-diol, 1,3-butylene glycol, cyclohexanediol, cyclohexane-1,4-dimethanol, hexane-1,6-diol, neopentyl glycol, hydroquinone dihydroxyethyl ether, bisphenol A (2,2-bis(4-hydroxyphenyl)propane), hydrogenated bisphenol A (2,2-bis(4-hydroxycyclohexyl)propane), trimethylolpropane, trimethylolethane, glycerol, pentaerythritol and any desired mixtures thereof with one another.

In a preferred embodiment of the invention, the preferably amorphous polyurethaneurea used in accordance with the invention contains ≤10% by weight of component E), preferably ≤5% by weight of component E), based in each case on the total mass of the preferably amorphous polyurethaneurea. Preferably, the preferably amorphous polyurethaneurea includes component E) within a range from 0.1% to 10% by weight, preferably within a range from 0.2% to 8% by weight, preferably within a range from 0.1% to 5% by weight, based in each case on the total mass of the preferably amorphous polyurethaneurea. In a further preferred embodiment, component E) is not used for preparation of the preferably amorphous polyurethaneurea.

In a preferred embodiment, the preferably amorphous polyurethaneurea used in accordance with the invention is prepared using ≥0.5% and ≤20% by weight of the sum total of components C1) and any E) and more preferably ≥1% and ≤15% by weight of the sum total of components C1) and any E), based in each case on the total mass of the preferably amorphous polyurethaneurea.

As component F) is possible to use further polymeric polyols that are different than B).

Preference is given to polymeric polyols not covered by the definition of B) because they are not polyetherpolyols—for example the following polyols that are known per se in polyurethane coating technology: polyesterpolyols, polyacrylatepolyols, polyurethanepolyols, polycarbonatepolyols, polyesterpolyacrylatepolyols, polyurethanepolyacrylatepolyols, polyurethanepolyesterpolyols, polyurethanepolycarbonatepolyols and polyesterpolycarbonatepolyols.

Preferably, component F) does not comprise polymeric polyols having ester groups, especially not polyesterpolyols.

According to the invention, components B) and F) together contain ≤30% by weight, preferably ≤10% by weight and more preferably ≤5% by weight of component F), based on the total mass of components B) and F). Most preferably, component F) is not used for preparation of the preferably amorphous polyurethaneurea.

In a preferred embodiment, the preferably amorphous polyurethaneurea used in accordance with the invention is prepared using ≥55% and ≤90% by weight of the sum total of components B) and any F) and more preferably ≥60% and ≤85% by weight of the sum total of components B) and any F), based in each case on the total mass of the preferably amorphous polyurethaneurea.

Component G) preferably comprises compounds having exactly one isocyanate-reactive group or compounds having more than one isocyanate-reactive group, where only one of the isocyanate-reactive groups reacts with isocyanate groups present in the reaction mixture under the reaction conditions chosen.

The isocyanate-reactive groups of component G) may be any functional group that can react with an isocyanate group, for example hydroxyl groups, thiol groups or primary and secondary amino groups.

Isocyanate-reactive groups in the context of the invention are especially preferably primary or secondary amino groups that react with isocyanate groups to form urea groups. As well as the amino group, compounds of component G) may also have other groups that are isocyanate-reactive in principle, for example OH groups, where just one of the isocyanate-reactive groups reacts with the isocyanate groups present in the reaction mixture under the reaction conditions chosen. This can be effected, for example, by reaction of appropriate amino alcohols at relatively low temperatures, for example at 0 to 60° C., preferably at 20 to 40° C. Preference is given here to working in the absence of catalysts that would catalyze the reaction of isocyanate groups with alcohol groups.

Examples of suitable compounds of component G) are primary/secondary amines, such as methylamine, ethylamine, propylamine, butylamine, octylamine, laurylamine, stearylamine, isononyloxypropylamine, dimethylamine, diethylamine, dipropylamine, dibutylamine, n-methylaminopropylamine, diethyl(methyl)aminopropylamine, morpholine, piperidine, diethanolamine, 3-amino-1-methylaminopropane, 3-amino-1-ethylaminopropane, 3-amino-1-cyclohexylaminopropane, 3-amino-1-methylaminobutane, ethanolamine, 3-aminopropanol or neopentanolamine Suitable monofunctional compounds are also ethanol, n-butanol, ethylene glycol monobutyl ether, diethylene glycol monomethyl ether, diethylene glycol monobutyl ether, propylene glycol monomethyl ether, dipropylene glycol monomethyl ether, tripropylene glycol monomethyl ether, dipropylene glycol monopropyl ether, propylene glycol monobutyl ether, dipropylene glycol monobutyl ether, tripropylene glycol monobutyl ether, 2-ethylhexanol, 1-octanol, 1-dodecanol, 1-hexadecanol.

In a preferred embodiment, the preferably amorphous polyurethaneurea used in accordance with the invention is prepared using ≥0.1% and ≤20% by weight of component G) and more preferably ≥0.3% and ≤10% by weight of component G), based in each case on the total mass of the preferably amorphous polyurethaneurea.

In a particularly preferred embodiment of the invention, component H) is used and the molar ratio of component G) to component H) is preferably 5:1 to 1:5, more preferably 1.5:1 to 1:4 and most preferably 1:1 to 1:3.

In a preferred embodiment, the preferably amorphous polyurethaneureas used in accordance with the invention are prepared using components A) to H) in the following amounts, where the individual amounts always add up to 100% by weight:
5% to 40% by weight of component A),
55% to 90% by weight of the sum total of components B) and optionally F),
0.5% to 20% by weight of the sum total of components C1) and optionally E),
0.1% to 10% by weight of component C2),
0% to 20% by weight of component D),
0.1% to 20% by weight of component G) and
0% to 10% by weight of component H).

In a particularly preferred embodiment, the preferably amorphous polyurethaneureas used in accordance with the invention are prepared using components A) to H) in the following amounts, where the individual amounts always add up to 100% by weight:
10% to 35% by weight of component A),
60% to 85% by weight of the sum total of components B) and optionally F),
1% to 15% by weight of the sum total of components C1) and optionally E),
0.5% to 4% by weight of component C2),
0% to 10% by weight of component D),
0.3% to 10% by weight of component G) and
0.1% to 3% by weight of component H).

In a preferred embodiment of the invention, the preferably amorphous adhesive comprises a preferably amorphous polyurethaneurea obtainable by reaction of at least
A) one aliphatic, cycloaliphatic or araliphatic polyisocyanate component having an average isocyanate functionality of ≥1.8 and ≤2.6, selected from HDI, IPDI and/or H12-MDI or modification products thereof,
B) a polymeric polyetherpolyol component preferably consisting of poly(propylene glycol) polyetherpolyols,
C) one amino-functional chain extender component having at least 2 isocyanate-reactive primary and/or secondary amino groups, containing at least one amino-functional compound C1) that does not have any ionic or ionogenic groups and/or an amino-functional compound C2) that has ionic or ionogenic groups,
D) optionally further hydrophilizing components different than C2),
E) optionally hydroxy-functional compounds having a molecular weight of 62 to 399 mol/g,
F) optionally further polymers polyols different than B),
G) optionally one compound having exactly one isocyanate-reactive group or one compound having more than one isocyanate-reactive group, where only one of the isocyanate-reactive groups reacts with the isocyanate groups present in the reaction mixture under the reaction conditions chosen, and
H) optionally one aliphatic, cycloaliphatic or araliphatic polyisocyanate component having an average isocyanate functionality of >2.6 and ≤4, where component H) consists of an aliphatic or cycloaliphatic polyisocyanate oligomer having isocyanurate, urethane, allophanate, biuret, iminooxadiazinedione or oxadiazinetrione structure, where components B) and F) together contain ≤30% by weight of component F), based on the total mass of components B) and F).

In a particularly preferred embodiment of the invention, the preferably amorphous adhesive comprises a preferably amorphous polyurethaneurea obtainable by reaction of at least
A) one aliphatic polyisocyanate component which is a mixture of IPDI and HDI,
B) one polymeric polyetherpolyol component which is a mixture of at least two poly(propylene glycol) polyetherpolyols and where the poly(propylene glycol) polyetherpolyols differ in their number-average molecular weights,
C) one amino-functional chain extender component having 2 isocyanate-reactive primary and/or secondary amino groups, containing at least one amino-functional compound C1) that does not have any ionic or ionogenic groups and/or an amino-functional compound C2) that has ionic or ionogenic groups,
D) optionally further hydrophilizing components that are different from C2), which are nonionically hydrophilizing components D1),
E) optionally hydroxy-functional compounds having a molecular weight of 62 to 399 mol/g,
F) optionally further polymeric polyols that are different than B),
G) optionally one compound having exactly one isocyanate-reactive group or one compound having more than one isocyanate-reactive group, where only one of the isocyanate-reactive groups reacts with the isocyanate groups present in the reaction mixture under the reaction conditions chosen, where the isocyanate-reactive group is a primary and/or secondary amino and/or hydroxyl group, and
H) optionally one aliphatic polyisocyanate component having an average isocyanate functionality of >2.6 and ≤4, where component H) consists of an aliphatic or cycloaliphatic polyisocyanate oligomer having isocyanurate, urethane, allophanate, biuret, iminooxadiazinedione or oxadiazinetrione structure, based on HDI, IPDI and/or H12-MDI, where components B) and F) together contain ≤30% by weight of component F), based on the total mass of components B) and F).

Preferably, the preferably amorphous polyurethaneurea used in accordance with the invention is obtainable by reacting exclusively components A) to H). In that case, no further components are used for preparation of the preferably amorphous polyurethaneurea.

The preferably amorphous polyurethaneureas used in accordance with the invention are preferably linear molecules, but may alternatively also be branched.

The number-average molecular weight of the preferably amorphous polyurethaneureas used with preference is preferably from ≥2000 to ≤300 000 g/mol, preferably from ≥5000 to ≤150 000 g/mol, or preferably from ≥10 000 to ≤100 000 g/mol.

The preferably amorphous polyurethaneurea used for production of the adhesive is preferably in a physiologically acceptable medium. The medium is more preferably water, and the preferably amorphous polyurethaneurea is most preferably in the form of an aqueous dispersion including essentially no further solvents. According to the invention, "essentially no further solvents" is understood to mean that less than 2% by weight, preferably less than 1.5% by weight, preferably less than 1% by weight, based on the total weight of the polyurethane dispersion, of further solvents are present in the polyurethane dispersion, especially no organic solvents, for example acetone. In general, alongside other liquid media that are optionally present, for example solvents, water generally forms the main constituent (>50% by weight) of the dispersion medium, based on the total amount of the liquid dispersion medium, and possibly even the sole liquid dispersion medium. Preferably, the preferably amorphous polyurethaneurea used is therefore dispersible in water, which means in the context of this invention that the preferably amorphous polyurethaneurea at 23° C. can form a sedimentation-stable dispersion in water, especially deionized water.

In a preferred embodiment of the adhesive, the preferably amorphous polyurethaneureas used are obtainable by preparing isocyanate-functional polyurethane prepolymers a) from components A), B) and optionally D) and/or C2), and optionally compounds E) and/or H) (step a), and then wholly or partially reacting the free NCO groups thereof with the amino-functional chain-extender component C), and also component G) and optionally components D) and H) (step b).

But when component H) is not used until step b), it is preferably added prior to the addition of component C) and reacted with the prepolymer a).

In a preferred embodiment of the invention, in step b), reaction is effected with a diamine or multiple diamines (component C) with chain extension, also with addition of the monofunctional component G) as chain terminator to control the molecular weight.

Components A) to H) are defined here as specified above. The abovementioned preferred embodiments are also applicable.

Preferably, in step b), the reaction of the prepolymer a) for preparation of the preferably amorphous polyurethaneurea, a mixture of components C1), C2) and G) is reacted. The use of component C1) can result in formation of a high molar mass without a rise in the viscosity of the isocyanate-functional prepolymer prepared beforehand to a degree that would be a barrier to processing. The use of the combination of components C1), C2) and G) can establish an optimal balance between hydrophilicity and chain length.

Preferably, the polyurethane prepolymer a) used in accordance with the invention has terminal isocyanate groups, meaning that the isocyanate groups are at the chain ends of the prepolymer. More preferably, all chain ends of the prepolymer have isocyanate groups.

The hydrophilizing components C2) and/or D) can be used to control the hydrophilicity of the prepolymer. In addition, further components are of course also significant for the hydrophilicity of the prepolymer, especially also the hydrophilicity of component B).

Preferably, the isocyanate-functional polyurethane prepolymers a) are water-insoluble and non-water-dispersible.

In the context of the invention, the term "water-insoluble, non-water-dispersible polyurethane prepolymer" means more particularly that the water solubility of the prepolymer used in accordance with the invention at 23° C. is less than 10 g/liter, preferably less than 5 g/liter, and the prepolymer at 23° does not result in any sedimentation-stable dispersion in water, especially deionized water. In other words, the prepolymer settles out when an attempt is made to disperse it in water. The water solubility or lack of dispersibility in water relates to deionized water without addition of surfactants.

Moreover, the polyurethane prepolymer a) used preferably has essentially neither ionic groups nor ionogenic groups (groups capable of forming ionic groups). In the context of the present invention, this means that the proportion of the ionic and/or ionogenic groups, such as anionic groups in particular, such as carboxylate or sulfate, or of cationic groups is less than 15 milliequivalents per 100 g of polyurethane prepolymer al), preferably less than 5 milliequivalents, more preferably less than 1 milliequivalent and most preferably less than 0.1 milliequivalent per 100 g of polyurethane prepolymer a).

In the case of acidic ionic and/or ionogenic groups, the acid number of the prepolymer is appropriately below 30 mg KOH/g of prepolymer, preferably below 10 mg KOH/g of prepolymer. The acid number indicates the mass of potassium hydroxide in milligrams required to neutralize 1 g of the sample to be examined (measurement to DIN EN ISO 211). The neutralized acids, i.e. the corresponding salts, naturally have a zero or reduced acid number. What is crucial here in accordance with the invention is the acid number of the corresponding free acid.

The water-insoluble, non-water-dispersible isocyanate-functional polyurethane prepolymers a) here are preferably obtainable exclusively from components A), B) and optionally D), E) and/or H).

The components are defined here as specified above. The abovementioned preferred embodiments are also applicable.

Consequently, in this embodiment, preference is given to using no ionically hydrophilizing components C2) or else D2) for preparation of the prepolymer a). Nor is component G) added in this step. The hydrophobizing agents D1) are preferably used in such amounts that the prepolymer is nevertheless water-insoluble and non-water-dispersible. More preferably ≤10% by weight of component D1), even more preferably ≤5% by weight and further preferably ≤2% by weight of component D1) is used, based in each case on the total mass of the preferably amorphous polyurethaneurea. Further preferably, component D1) is not used for preparation of the prepolymer a).

In a preferred embodiment of the invention, component B) has neither ionic nor ionogenic groups. In addition, in this embodiment of the invention, preference is given to using, as component B), polyetherpolyols only, especially polyalkylene oxide ethers containing ≤10 mol % and, based on all alkylene oxide units present, of ethylene oxide units and preferably no ethylene oxide units.

The preferably amorphous polyurethaneureas used with preference in this embodiment of the invention consequently have ionic or ionogenic groups, preferably anionic groups; these anionic groups are introduced into the preferably amorphous polyurethaneureas used via the hydrophilizing component C2) used in step b). The preferably amorphous polyurethaneureas used optionally additionally include non-ionic components for hydrophilization.

More preferably, the preferably amorphous polyurethaneureas used, for hydrophilization, contain exclusively sulfonate groups that are introduced into the preferably amorphous polyurethaneurea in step b) via corresponding diamines as component C2).

In an alternative, less preferred embodiment of the invention, the prepolymers a) used for preparation of the preferably amorphous polyurethaneureas of the invention are water-soluble or water-dispersible. In this embodiment, the hydrophilizing components D) and/or C2) are used in the preparation of the prepolymer a) in an amount sufficient for the prepolymer to be water-soluble or water-dispersible. The prepolymer a) here preferably has ionic or ionogenic groups.

Suitable hydrophilizing components D) and C2) for this embodiment of the invention are the compounds mentioned above for D) and C2). The hydrophilizing components used are at least the compounds mentioned above under D1) and/or C2).

The preferably amorphous polyurethaneureas used for production of the adhesive of the invention are preferably dispersed in water before, during or after step b), more preferably during or after step b). In this way, a dispersion of the preferably amorphous polyurethaneureas is obtained.

The production of the preferably amorphous polyurethaneurea dispersions can be conducted here in one or more stage(s) in a homogeneous reaction or in a multistage reaction, partly in disperse phase. Preparation of the prepolymer a) is preferably followed by a dispersion, emulsification or dissolution step. This is optionally followed by a further polyaddition or modification in disperse phase. In this case, the solvent or dispersant suitable for the corresponding prepolymer in each case, for example water or acetone or mixtures thereof, is chosen.

It is possible here to use any methods known from the prior art, for example prepolymer mixing methods, acetone methods or melt dispersion methods. Preference is given to employing the acetone method.

For preparation by the acetone method, it is customary to wholly or partly initially charge constituents B), optionally D) and E) and the polyisocyanate component A), optionally in combination with component H) for preparation of an isocyanate-functional polyurethane prepolymer, and optionally to dilute them with a solvent which is water-miscible but inert toward isocyanate groups, and to heat them to temperatures in the range from 50 to 120° C. The isocyanate addition reaction can be accelerated using the catalysts known in polyurethane chemistry.

Suitable solvents are the customary aliphatic keto-functional solvents, such as acetone, 2-butanone, which can be added not just at the start of the preparation but optionally also in portions at a later stage. Preference is given to acetone and 2-butanone, particular preference to acetone. The addition of other solvents without isocyanate-reactive groups is also possible, but not preferred.

Subsequently, any constituents of A), B) and optionally H), D) and E) which have not yet been added at the start of the reaction can be metered in.

In the preparation of the polyurethane prepolymer from A), B) and optionally H), D) and E), the molar ratio of isocyanate groups to isocyanate reactive groups is preferably 1.05 to 3.5, more preferably 1.1 to 3.0 and most preferably 1.1 to 2.5.

The conversion of components A), B) and optionally H), D) and E) to the prepolymer can be effected in part or in full, but preferably in full. In this way, polyurethane prepolymers containing free isocyanate groups can be obtained in neat form or in solution.

If ionogenic groups, for example carboxyl groups, should be present in the prepolymer, these can be converted to ionic groups by neutralization in a further step.

In the neutralization step, for partial or complete conversion of potentially anionic groups to anionic groups, it is possible to use bases such as tertiary amines, e.g. trialkylamines having 1 to 12 and preferably 1 to 6 carbon atoms, more preferably 2 to 3 carbon atoms, in each alkyl radical, and most preferably alkali metal bases such as the corresponding hydroxides.

Usable neutralizing agents are preferably inorganic bases, such as aqueous ammonia solution or sodium hydroxide or potassium hydroxide; particular preference is given to sodium hydroxide and potassium hydroxide.

The molar amount of the bases is preferably 50 and 125 mol %, more preferably between 70 and 100 mol %, of the molar amount of the acid groups to be neutralized. Neutralization can also be effected simultaneously with the dispersion, in that the dispersion water already contains the neutralizing agent.

After the neutralization, in a further process step, if this has been done only partly, if at all, the prepolymer obtained is dissolved with the aid of aliphatic ketones such as acetone or 2-butanone.

In the chain extension/termination in stage b), components C), G) and optionally D) are reacted with the isocyanate groups still remaining in the prepolymer. Preference is given to conducting the chain extension/termination prior to the dispersion in water.

Suitable components C) for chain extension and G) for chain termination have already been listed above. The abovementioned preferred embodiments are also applicable analogously.

If anionic hydrophilizing agents in accordance with definition C2) having $NH_2$ groups or NH groups are used for chain extension, the chain extension of the prepolymers in step b) is preferably effected prior to the dispersion in water.

The equivalents ratio of NCO-reactive groups in the compounds used for chain extension and chain termination to free NCO groups in the prepolymer is generally between 40% and 150%, preferably between 50% and 110%, more preferably between 60% and 100%.

Components C1), C2) and G) may optionally be used in water- or solvent-diluted form in the process of the invention, individually or in mixtures, any sequence of addition being possible in principle.

When water or organic solvent is included as diluent in step b), the respective diluent content in components C1), C2) and G) used is preferably 40% to 95% by weight.

Dispersion preferably follows after the chain extension and chain termination. For this purpose, the polyurethane polymer that has been dissolved (for example in acetone) and reacted with the amines is either introduced into the dispersion water, optionally under high shear, for example vigorous stirring, or, conversely, the dispersion water is stirred into the chain-extended polyurethane polymer solutions. Preferably, the water is added to the dissolved polyurethane polymer.

The solvent still present in the dispersions after the dispersion step is typically then removed by distillation. Removal even during the dispersion is likewise possible.

The aqueous polyurethaneurea dispersions obtained preferably have a content of volatile organic compounds (VOCs), for example volatile organic solvents, of less than 10% by weight, more preferably of less than 3% by weight, even more preferably of less than 1% by weight, based on the aqueous polyurethaneurea dispersion. VOCs in the context of this invention are especially organic compounds having an initial boiling point of at most 250° C. at a standard pressure of 101.3 kPa.

In the context of the present invention, the content of volatile organic compounds (VOCs) is especially determined by gas chromatography analysis.

The pH of the aqueous polyurethane dispersions used is typically less than 8.0, preferably less than 7.5, and is more preferably between 5.5 and 7.5.

In order to achieve good sedimentation stability, the number-average particle size of the specific polyurethaneurea dispersions is preferably less than 750 nm, more preferably less than 500 nm, determined by means of laser correlation spectroscopy after dilution with deionized water (instrument: Malvern Zetasizer 1000, Malvern Inst. Limited).

The solids content of the polyurethaneurea dispersions is preferably 10% to 70% by weight, more preferably 20% to 60% by weight and most preferably 40% to 60% by weight. The solids contents are ascertained by heating a weighed sample to 125° C. to constant weight. At constant weight, the solids content is calculated by reweighing the sample.

Preferably, these polyurethaneurea dispersions include less than 5% by weight, more preferably less than 0.2% by weight, based on the mass of the dispersions, of unbound organic amines The polyurethaneurea dispersions used for production of the adhesive have, at 23° C., at a constant shear rate of 10 $s^{-1}$, preferably a viscosity of ≥1 and ≤10 000 mPa s, more preferably of ≥10 and ≤5000 mPa s and most preferably of ≥100 and ≤4000 mPa s. The viscosity is determined as described in the Methods section.

The polyurethaneurea used for the production of the adhesive is preferably amorphous. In a preferred embodiment of the adhesive, the polyurethaneurea used has a $T_g$ of ≤−25° C., or preferably of ≤−50° C., or preferably of ≤−70° C.

"Amorphous" in the context of this invention means that the polyurethaneurea, within the temperature range specified in the test method detail hereinafter, forms only such minor crystalline components, if any, that, by means of the DSC measurements described, it is possible to find only one or more glass transition points $T_g$ but no fusion regions having an enthalpy of fusion ≥20 J/g within the temperature range mentioned.

The glass transition temperature $T_g$ is determined in the context of this invention by means of dynamic differential calorimetry in accordance with DIN EN 61006, Method A, using a DSC instrument calibrated with indium and lead for determination of $T_g$, by conducting three directly consecutive runs composed of heating operations from −100° C. to +150° C., with a heating rate of 20 K/min, in each case with subsequent cooling at a cooling rate of 320 K/min, and using the third heating curve to determine the values and determining $T_g$ as the temperature at half the height of a glass transition step.

If the polyurethaneurea should be in the form of a dispersion, a special procedure is followed in the sample preparation for the DSC measurements. In the determination of the glass transition temperature $T_g$ of dispersions by means of DSC, the $T_g$ of the polymer can be masked by the caloric effects of the dispersant (water, neutralizing agent, emulsifier, cosolvent etc.) or distinctly lowered owing to miscibility with the polymer. Therefore, the dispersant, prior to the DSC measurement, is preferably first removed completely by suitable drying, since even small residual amounts of dispersant act as plasticizer and can lower the glass transition temperature as a result. The dispersion is therefore preferably knife-coated onto a glass plate at wet film thickness (WFT) 200 μm with a stainless steel applicator frame, flashed off and then dried gently in a dry box at RT and 0% relative air humidity (rh) for two days. After this sample preparation, in the first heating operation in the DSC measurement, it is still possible for a broad endothermic evaporation range of residual moisture in the film to occur. In order to keep the determined values free of such influences as far as possible, the third heating curve is therefore evaluated.

Component I) is preferably selected from the group of low molecular weight aliphatic diisocyanates of molar mass from 140 to 278 g/mol and polyisocyanates preparable therefrom and having an isocyanate functionality of 2 to 3.6, or preferably of 2 to 3, or mixtures of at least two of these.

Component J) is preferably a monofunctional polyalkylene oxide of OH number from 10 to 250, or preferably from 15 to 220, or preferably from 20 to 200. The polyalkylene oxide is preferably selected from the group consisting of ethylene oxide, propylene oxide, butylene oxide, pentylene oxide or a mixture of at least two of these. The polyalkylene oxide component preferably has an ethylene oxide content of 50 to 100 mol % based on the total amount of the oxyalkylene groups present.

In the preparation of a hydrophilic polyisocyanates K2., the ratio of the monofunctional polyalkylene oxides J) to the low molecular weight aliphatic diisocyanates I) is typically adjusted such that, for every 1 mol of OH groups of the monofunctional polyalkylene oxides, there are 1.25 to 20 mol, preferably 2 to 15 mol, or preferably 5 to 13 mol, of NCO groups in the low molecular weight aliphatic diisocyanate I). This is preferably followed by the allophanatization or biuretization and/or isocyanurate formation or uretdione formation. If the polyalkylene oxides J) are bonded to the aliphatic diisocyanates I) via urethane groups, this is preferably followed by an allophanatization. It is further preferable that isocyanate structural units are formed.

A preferred alternative preparation of the hydrophilic polyisocyanates K2. is typically affected by reacting 1 mol of OH groups of the monofunctional polyalkylene oxide component J) with 1.25 to 20 mol, preferably with 2 to 15 mol and more preferably 5 to 13 NCO groups of a polyisocyanate I) having an isocyanate functionality of 2 to 3.6, based on aliphatic diisocyanates. Examples of such polyisocyanurates I) are biuret structures, isocyanurates or uretdiones based on aliphatic diisocyanates.

This preferably involves joining the polyisocyanate I) and the polyalkylene oxide J) to one another, preferably via a urethane group or a urea group, particular preference being given to joining via urethane groups.

The reaction can be effected in the presence of urethanization catalysts such as tin compounds, zinc compounds, amines, guanidines or amidines, or in the presence of allophanatization catalysts such as zinc compounds.

The reaction is typically effected at 25 to 140° C., preferably 60 to 100° C.

If excess low molecular weight diisocyanate has been employed, this is followed by the removal of the excess of low molecular weight aliphatic diisocyanate, preferably by thin-film distillation.

Before, during and/or after the reaction of the distillative removal of the diisocyanate excess, it is possible to add acidic or alkylating stabilizers such as benzoyl chloride, isophthaloyl chloride, methyl tosylate, chloropropionic acid, HCl or antioxidants such as di-tert-butylcresol or tocopherol.

The NCO content of the hydrophilic polyisocyanates K2. is preferably 0.3% to 23% by weight, more preferably 2% to 21% by weight and most preferably 3% to 18% by weight.

Examples of low molecular weight aliphatic diisocyanates of component I) are hexamethylene diisocyanate (HDI), isophorone diisocyanate (IPDI), butylene diisocyanate (BDI), pentamethylene isocyanate (PDI), bisisocyanatocyclohexylmethane (HMDI), 2,2,4-trimethylhexamethylene diisocyanate, bisisocyanatomethylcyclohexane, bisisocyanatomethyltricyclodecane, xylene diisocyanate, tetramethylxylylene diisocyanate, norbornane diisocyanate, cyclohexane diisocyanate or diisocyanatododecane, preference being given to hexamethylene diisocyanate (HDI), isophorone diisocyanate (IPDI), butylene diisocyanate (BDI), pentamethylene isocyanate (PDI), and bis(isocyanatocyclohexyl)methane (HMDI). Particular preference is given to BDI, HDI, IPDI, very particular preference to hexamethylene diisocyanate and isophorone diisocyanate.

Examples of higher molecular weight polyisocyanates I) are polyisocyanates having an isocyanate functionality of 2 to 3.6 with isocyanurate, urethane, allophanate, biuret, iminooxadiazinetrione, oxadiazinetrione and/or uretdione groups based on the aliphatic and/or cycloaliphatic diisocyanates mentioned in the previous paragraph.

Components I) used are preferably higher molecular weight compounds having biuret, iminooxadiazinedione, isocyanurate and/or uretdione groups based on hexamethylene diisocyanate, isophorone diisocyanate and/or 4,4'-diisocyanatodicyclohexylmethane. Isocyanurates are further preferred. Very particular preference is given to structures based on hexamethylene diisocyanate.

The monofunctional polyalkylene oxides J) have an OH number of 15 to 250, preferably of 28 to 112, and an ethylene oxide content of 50 to 100 mol %, preferably of 60 to 100 mol %, based on the total amount of the oxyalkylene groups present.

Monofunctional polyalkylene oxides in the context of the invention are understood to mean compounds that have just one isocyanate-reactive group, i.e. one group that can react with an NCO group.

The preparation of polyalkylene oxides J) by alkoxylation of suitable starter molecules is known from the literature (e.g. Ullmanns Encyclopadie der technischen Chemie [Ullmann's Encyclopedia of Industrial Chemistry], 4th edition, volume 19, Verlag Chemie, Weinheim p. 31-38). Suitable starter molecules are especially saturated monoalcohols such as methanol, ethanol, n-propanol, isopropanol, n-butanol, isobutanol, sec-butanol, diethylene glycol monobutyl ether and aromatic alcohols such as phenol or monoamines such as diethylamine Preferred starter molecules are saturated monoalcohols of the aforementioned type. Particular preference is given to using diethylene glycol monobutyl ether or n-butanol as starter molecules.

The monofunctional polyalkylene oxides J) typically have number-average molecular weights of 220 to 3700 g/mol, preferably of 250 to 2800 g/mol, or preferably of 300 to 2000 g/mol.

The monofunctional polyalkylene oxides J) preferably have one OH group as isocyanate-reactive group.

In a preferred embodiment of the adhesive:
I) is selected from the group consisting of
  I1.) low molecular weight aliphatic diisocyanates of molar mass from 140 to 278 g/mol;
  I2.) polyisocyanates preparable from I1.) and having an isocyanate functionality of 2 to 3.6;
  I3.) combination of I1.) and I2.);
J) is selected from the group consisting of
  J1.) a monofunctional polyalkylene oxide of OH number from 10 to 250;
  J2.) ethylene oxide, propylene oxide, butylene oxide, pentylene oxide or a mixture of at least two of these;
  J3.) a monofunctional polyalkylene oxide having an ethylene oxide content of 50 to 100 mol % based on the total amount of oxyalkylene groups present
  J4.) a combination of at least two of J1.) to J3.).

Typical further suitable admixtures and auxiliaries L) are surface additives, for example wetting agents, dyes and/or leveling aids.

The polyurethaneurea dispersion may also contain all other admixtures known to the person skilled in the art for the respective application.

The invention further provides an aqueous polyurethaneurea dispersion, comprising
  (V1) an amorphous polyurethaneurea obtainable by reacting at least
  A) one aliphatic, cycloaliphatic or araliphatic polyisocyanate component having an average isocyanate functionality of ≥1.8 and ≤2.6,
  B) one polymeric polyetherpolyol component,
  C) one amino-functional chain extender component having at least 2 isocyanate-reactive amino groups, containing at least one amino-functional compound C1) that does not have any ionic or ionogenic groups and/or an amino-functional compound C2) that has ionic or ionogenic groups,
  D) optionally further hydrophilizing components different than C2),
  E) optionally hydroxy-functional compounds having a molecular weight of 62 to 399 mol/g,
  F) optionally further polymeric polyols that are different than B),
  G) optionally one compound having exactly one isocyanate-reactive group or one compound having more than one isocyanate-reactive group, where only one of the isocyanate-reactive groups reacts with the isocyanate groups present in the reaction mixture under the reaction conditions chosen, and
  H) optionally one aliphatic, cycloaliphatic or araliphatic polyisocyanate component having an average isocyanate functionality of >2.6 and ≤4,
  where components B) and F) together contain ≤30% by weight of component F), based on the total mass of components B) and F),
  and
  (V2) a hydrophilic polyisocyanate preparable from
  I) an aliphatic, cycloaliphatic or araliphatic polyisocyanate component having an average isocyanate functionality of preferably ≥2.0 and ≤3.6,
  J) a polymeric, hydrophilic and monofunctional polyalkylene oxide component, K) optionally further hydrophilizing components different than J), L) optionally admixtures and auxiliaries.

Preferably, components A) to L) are the same as the selections for the adhesive that have been detailed for the corresponding components. All the properties, amounts, ratios and compositions with regard to components A) to L) that have been detailed in connection with the adhesive are likewise applicable to the polyurethaneurea dispersion and the hydrophilic polyisocyanate used.

The invention further relates to a process for producing a layer construction including at least one adhesive layer, comprising the steps of:

(I) mixing a hydrophilic polyisocyanate (V2) into a polyurethaneurea (V1) to obtain a polyurethaneurea dispersion of the invention, (II) applying the polyurethaneurea dispersion to a first further layer to obtain a precursor, (III) thermally treating the precursor from step (I) at temperatures within a range from 20° C. to 200° C. to form the adhesive layer.

The adhesive layer produced in the process is preferably configured like the adhesive layer described above. Preferably, the adhesive layer produced by the process of the invention has the same materials, properties and configurations as already described for the adhesive layer of the invention.

The mixing of the hydrophilic polyisocyanate (V2) into the polyurethaneurea dispersion (V1) to obtain a polyurethaneurea mixture can be effected in any manner that the person skilled in the art would select for the purpose. The mixing preferably takes place with the aid of a stirrer or a mixer or a combination of the two. Preferably, the mixing is conducted at such a mixing rate that homogeneous mixing of components (V1) and (V2) into the polyurethaneurea mixture is effected within a few minutes, preferably within fewer than 5 minutes, more preferably within fewer than 3 minutes.

The mixing at least of components (V1) and (V2) in the form of the adhesive preferably has sufficiently long processibility to be able to process the mixture to give the desired product in the form of the adhesive. Sufficiently long processibility exists at least when the mixture is pourable out of a reservoir vessel exclusively due to gravity. The mixture can preferably be applied to a substrate in the form of the first further layer within 8 hours after mixing. Within this period of sufficiently long processibility, component (V2) can dwell in a mixture with (V1) after step (I) without reacting to such a degree that no further crosslinking takes place after production of the film in step (II).

The preferably amorphous polyurethaneurea can be applied to the first further layer in step (II) by means of any method that the person skilled in the art would select for the purpose. Preferably, the applying of the preferably amorphous polyurethaneurea in the form of the aqueous polyurethaneurea dispersion takes place by a method selected from the group consisting of printing, brushing, knife coating, spraying, coating by other known coating methods. The polyurethaneurea dispersion can be applied to the first further layer in multiple laminas. The polyurethaneurea dispersion is preferably applied to the first further layer in 1 to 10 laminas, or preferably in 2 to 10 laminas, or preferably in 3 to 10 laminas. The first further layer, on application of the polyurethaneurea dispersion, is preferably supported such that the polyurethaneurea dispersion is distributed with maximum homogeneity on the surface of the first further layer. After application of the polyurethaneurea dispersion to the first further layer, the precursor is obtained. Before it is supplied to the step (III) of the process, the precursor can be covered with a second further layer. However, the covering can also follow step (III) or take place during step (III).

Preferably, the viscosity of the polyurethaneurea dispersion, prior to the application in step (II), can be adjusted to the required circumstances by dilution or thickening or a combination of both methods in order to achieve desired application thicknesses. It is possible here to use thickeners as admixtures L) preferably in component (V2). Typical thickeners are soluble polyacrylate- or polyurethane-based polymers as known from the prior art. Preference is given to thickeners based on polyurethane polymers. The polyurethaneurea dispersion can be diluted using standard solvents, but preference is given to water.

Typical further suitable admixtures and auxiliaries L) are surface additives, for example wetting auxiliaries, dyes and/or leveling auxiliaries. The polyurethaneurea dispersion may also contain all further admixtures known to the person skilled in the art for the respective use.

The printing may include any method of printing the polyurethaneurea dispersion that the person skilled in the art would select for the purpose. The printing method is preferably selected from the group consisting of a screenprinting method, an inkjet method, an intaglio printing method, an offset printing method, a roll printing method, a gravure printing method or a combination of at least two of these. Examples of the inkjet printing method are the continuous inkjet printing method in which the material to be printed is applied to the substrate in a continuous jet, or drop-on-demand printing in which individual droplets are applied to the substrate to be printed. By all these printing methods, the polyurethaneurea dispersion can be applied over the full area or else part of the area. The polyurethaneurea dispersion can likewise be applied in a particular pattern, also referred to as "pattern coating". The dispersion can be applied here by all methods known to those skilled in the art, including and more particularly of gravure printing, screenprinting or inkjet printing.

Preferably, the polyurethaneurea dispersion is applied to the substrate, the first further layer or the second further layer here, with a coat weight within a range from 5 g/m² to 200 g/m².

For coating bar application, the first further layer is preferably fixed beforehand in a clamping apparatus and then the coating bar with the dispersion in front of it can be guided by hand or in an automated manner across the first further layer, and the dispersion can be distributed uniformly thereon. Coating can likewise be effected via a typical roll-to-roll coating system with a coating bar, in which the first further layer is coated continuously.

In the case of spray application, the first further layer is clamped, preferably in a frame, and sprayed with the dispersion on one or both sides from a spray gun. Application can be effected in one or more cross-coating operations, manually or by means of a continuous roll-to-roll spray system.

The first further layer is preferably configured in the manner described for the first further layer in connection with the adhesive layer of the invention.

The thermal treatment in step (III) can be effected in any manner as would be selected by the person skilled in the art for the purpose. Preferably, the thermal treatment takes place with employment of elevated temperature relative to room temperature. The thermal treatment can take place at any site suitable for the purpose. The thermal treatment preferably takes place in a space selected from the group consisting of a drying space, a drying oven, a drying tube, or a combination of at least two of these. Thermal drying can be replaced or assisted by IR or microwave drying. According to the invention, the thermal treatment takes place at a temperature within a range from 20° C. to 200° C., preferably within a range from 30° C. to 200° C., or preferably within a range from 50° C. to 200° C., or preferably within a range from 80° C. to 200° C., or preferably within a range from 20° C. to 180° C., or preferably within a range from 20° C. to 150° C., or preferably within a range from 20° C. to 100° C., or preferably within a range from 50° C. to 150° C. Preferably, the thermal treatment takes place for a period of time within a range from 1 minute to 10 hours, or preferably within a range from 10 minutes to 5 hours, or preferably within a range from 30 minutes to 2 hours. Preferably, a gas, preferably air, is passed over at least the surface of the polyurethaneurea dispersion, such that faster drying of the polyurethaneurea dispersion to give the adhesive layer is possible.

A preferred configuration of the above-described process comprises at least one of the following further steps:
(IV) detaching the adhesive layer from the first further layer;
(V) transferring the adhesive layer from the first further layer to a second further layer;
(VI) covering the adhesive layer with a second further layer on the first surface of the first layer;
(VII) covering the adhesive layer with a second further layer on the first further surface of the first layer;
(VIII) transferring the adhesive layer from the first further layer to a substrate;
(IX) transferring the adhesive layer from the first further layer to at least a portion of a component surface of a component;
(X) transferring the adhesive layer from the first further layer to a third further layer.

The detaching of the adhesive layer in step (IV) can be effected in any manner that the person skilled in the art would envisage for the purpose. The detaching of the adhesive layer in step (IV) is preferably effected by means of a spatula, preferably a wood, plastic or metal spatula.

The transferring of the adhesive layer from the first further layer to a second further layer in step (V) can be effected in any manner that the person skilled in the art would envisage for the purpose. The transferring of the adhesive layer in step (V) is preferably effected by placing a second further layer onto the uncovered part of the adhesive layer, with transfer of the adhesive layer by pressure on the first further layer. The pressure can be effected, for example, by turning over the adhesive layer, such that the second further layer bears the adhesive layer and comes to rest thereon by virtue of gravity alone when the first further layer is removed. Step (V) can likewise be effected by a translamination process, preferably in a continuous roll-to-roll process. The lamination step is preferably effected at temperatures between 5° C. and 200° C.

The covering of the adhesive layer with a second further layer atop the first surface of the first layer in step (VI) can be effected in any manner that the person skilled in the art would envisage for the purpose. The covering of the adhesive layer in step (VI) is preferably effected by placing or laminating a second further layer on the first surface of the first layer.

The covering of the adhesive layer with a second further layer atop the first surface of the first further layer in step (VII) can be effected in any manner that the person skilled in the art would envisage for the purpose. The covering of the adhesive layer in step (VII) is preferably effected by placing or laminating a second further layer on the first further surface of the first layer.

The transferring of the adhesive layer from the first further layer to a substrate in step (VIII) can be effected in any manner that the person skilled in the art would envisage for the purpose. The transferring of the adhesive layer in step (VIII) is preferably effected by placing the substrate onto the uncovered part of the adhesive layer, with transfer of the adhesive layer to the substrate by pressure on the first further layer. The pressure can be effected, for example, by turning over the adhesive layer, such that the substrate bears the adhesive layer and comes to rest thereon by virtue of gravity alone when the first further layer is removed. Preferably, an additional pressure is generated with the aid of an article on at least part of the first further layer, which brings about better adhesion of the adhesive layer on the substrate than on the first further layer. Step (VIII) is preferably effected by a translamination process, preferably by a continuous roll-to-roll process.

The transferring of the adhesive layer from the first further layer to at least part of a component surface of a component in step (IX) can be effected in any manner that the person skilled in the art would envisage for the purpose. The transferring of the adhesive layer in step (IX) is preferably effected by placing the component surface of the component onto the uncovered part of the adhesive layer, with transfer of the adhesive layer to the component by pressure on the first further layer. The pressure can be effected, for example, by turning over the adhesive layer, such that the component bears the adhesive layer and comes to rest thereon by virtue of gravity alone when the first further layer is removed. Preferably, an additional pressure is generated with the aid of an article on at least part of the first further layer, which brings about better adhesion of the adhesive layer on the substrate than on the first further layer. Step (IX) is preferably effected by a translamination process, preferably by a continuous roll-to-roll process.

The transferring of the adhesive layer from the first further layer to a third further layer in step (X) can be effected in any manner that the person skilled in the art would envisage for the purpose. The transferring of the adhesive layer in step (X) is preferably effected by placing the third further layer onto the uncovered part of the adhesive layer, with transfer of the adhesive layer by pressure on the first further layer. The pressure can be effected, for example, by turning over the adhesive layer, such that the third further layer bears the adhesive layer and comes to rest thereon by virtue of gravity alone when the first further layer is removed. Step (X) can likewise be effected by a translamination process, preferably in a continuous roll-to-roll process. The lamination step is preferably effected at temperatures between 5° C. and 200° C.

Preferably, the material, the properties and the shape of the third further layer are configured as described above for the first further layer. The third further layer is preferably of the same construction as the first or second further layer.

The invention further relates to the use of the adhesive of the invention or of the adhesive layer of the invention for securing of a product on an article or on the skin of a living being.

In the case of use of the adhesive of the invention, preferably at least one of the following steps is conducted:
The adhesive is contacted with the product. The adhesive, when contacted with the product, preferably adheres more to the product than to the first further layer, the second further layer or the third further layer on which the adhesive has been produced in the form of the adhesive layer or to which the adhesive has been transferred.

The product is contacted with a further article, a further part of the product or the skin of a user. After being contacted with the article, the further part of the product or the skin, the product preferably adheres sufficiently strongly to the surface thereof that it does not become detached therefrom again when the product is utilized as usual. Utilization as usual is understood to mean the use of the product as customary on the market as would be understood by the person skilled in the art. This includes all everyday tasks such as showering, normal movement, normal activities of the patient.

After its desired wearing time, the product is removed from the substrate with expenditure of a force within a range from 0.1 to 10.0 N/20 mm, preferably 0.15 to 5 N/20 mm. The substrate can also be the skin of the user.

Preferably, the product to be secured is one of the above-described products.

Preferably, the use of the adhesive of the invention takes place in and on a product in the medical sector, especially for securing of the product on the skin of a living being. Particularly within the field of medical applications, particularly of surgical applications, it is desirable to assure a good bonding force of the medical products to the skin of the living being, especially of the human or animal patient. Preferably, the medical product additionally has the following features:

(1) a dwell time on the skin within a range from 1 second to 180 days;
(2) a reduction in bonding force over the dwell time of 10 days of less than 50%, preferably of less than 30%, or preferably of less than 10%, based on the original bonding force.

The adhesive layer of the invention preferably forms an adhesive layer comprising
at least one first layer comprising at least one first surface and at least one first further surface, where the first surface runs essentially parallel to the first further surface,
wherein the first layer includes the above-described adhesive of the invention.

Preferably, the adhesive layer includes the adhesive within a range from 60% to 100% by weight, or preferably within a range from 70% to 100% by weight, or preferably within a range from 80% to 100% by weight, based on the total weight of the adhesive layer.

The adhesive layer preferably includes at least one further component within a range from 0% to 40% by weight, or preferably within a range from 0% to 30% by weight, or preferably within a range from 0% to 20% by weight, based on the total weight of the adhesive layer. Further preferably, the adhesive layer includes the further component within a range from 0.1% to 20% by weight, or preferably within a range from 0.5% to 15% by weight, or preferably within a range from 1% to 10% by weight, based on the total mass of the adhesive layer. The further component may be selected from the group consisting of water, a thickener, a diluent, a filler (such as calcite or talc), a dye, a superabsorbent (for example based on a polyacrylate or carboxymethylcellulose), an antimicrobial or pharmaceutically active substance (for example growth factors, peptides, painkillers, wound healing accelerators, silver, polyhexanide inter alia), a disinfectant, such as a bactericide or fungicide, or a combination of at least two of these.

The adhesive layer preferably has a thickness within a range from 2 μm to 20 mm, more preferably within a range from 5 μm to 10 mm, or preferably within a range from 10 μm to 2000 μm, or preferably within a range from 40 μm to 800 μm. The adhesive layer preferably has the same thickness over its entire, preferably two-dimensional, extent. The same thickness is understood in accordance with the invention to mean that the thickness over the entire adhesive layer does not deviate by more than 10% from the mean thickness of the adhesive layer. According to the invention, the average thickness of the adhesive layer is the average of the thickness values determined at the respective thinnest and thickest sites on the adhesive layer. The values for the determination of thickness are determinable by means of a conventional micrometer gauge.

The adhesive layer preferably has, in its greatest two-dimensional extent, a shape selected from the group consisting of round, polygonal, rectangular, square, elliptical, trapezoidal, rhombus-shaped or a combination of at least two of these. The adhesive layer is preferably rectangular or elliptical.

The adhesive layer preferably has a width within a range from 1 mm to 10 m, or preferably within a range from 1 cm to 10 m, or preferably within a range from 1 cm to 10 m, or preferably within a range from 1 mm to 5 m, or preferably within a range from 1 mm to 1 m, or preferably within a range from 5 mm to 5 m, or preferably within a range from 1 cm to 1 m.

The adhesive layer preferably has a length within a range from 2 mm to 100 m, or preferably within a range from 1 cm to 10 m, or preferably within a range from 10 cm to 10 m, or preferably within a range from 2 mm to 50 m, or preferably within a range from 2 mm to 10 m, or preferably within a range from 5 mm to 50 m, or preferably within a range from 1 cm to 10 m.

According to the invention, the adhesive layer has at least two surfaces: a first surface and a first further surface. According to the invention, the first surface and the first further surface run essentially parallel to one another. In the context of the invention, essentially parallel is understood to mean that the two surfaces do not touch at any point across the adhesive layer. Preferably, the two surfaces that run essentially parallel to one another, namely the first surface and the first further surface, are separated from one another at the edges of the adhesive layer by at least one second further surface. The extent of this second further surface at the perpendicular between the first surface and the first further surface forms the thickness of the adhesive layer at the edges thereof. Preferably, the first surface and the first further surface have a two-dimensional extent. Further preferably, the first surface and the first further surface have a virtually identical total area. A virtually identical total area is understood to mean a difference in the total areas of the first surface and the first further surface of not more than 50%, preferably not more than 30%, or preferably not more than 10%, or preferably not more than 5%, based on the total area of the first surface.

The shape of the surface of the first surface and/or of the first further surface is preferably selected from the group consisting of planar, curved, inflected or a combination of at least two of these. The first surface and/or the first further surface may each also extend over multiple, preferably two, three or four, adjoining faces. Preferably, the adjoining faces which the surface of the first surface and/or first further surface have an inclination relative to one another within a region of less than 45°, or preferably of less than 40°, or preferably of less than 30° relative to one another. The surface of the first surface and/or of the first further surface is preferably planar.

The total area of the first surface and/or of the first further surface is preferably within a range from 1 mm² to 1000 m², or preferably within a range from 100 mm² to 500 m², or preferably within a range from 1 cm² to 100 m².

The adhesive layer preferably has at least one of the following features:

a) steam permeability within a region of at least 800 g/d m², preferably ≥1200 g/d m² and more preferably ≥1500 g/d m².

b) a length and width corresponding to at least 10 times, preferably at least 20 times, or preferably at least 30 times, or preferably at least 40 times, or preferably at least 100 times, the thickness of the adhesive layer;

c) a bonding force within a region of ≥0.25 N/20 mm, or preferably of ≥0.5 N/20 mm, or preferably of ≥1.0 N/20 mm, or preferably of ≥1.3 N/20 mm (determined via 90° peel test against aluminum sheet, DIN EN 1464).

Preferably, the bonding forces determined in this way are within a range from 0.25 to 20 N/20 mm, or preferably from 0.5 to 15 N/20 mm, or preferably from 1.0 to 12.5 N/20 mm, or preferably from 1.3 to 12.0 N/20 mm, or preferably from 1.5 to 10.0 N/20 mm.

In a preferred configuration of the adhesive layer, the adhesive layer is at least partly covered on its first surface at least by a first further layer.

Preferably, the first further layer covers the first surface of the adhesive layer within a range from 50% to 100%, or preferably within a range from 60% to 100%, or preferably within a range from 70% to 100%, or preferably within a range from 80% to 100%, based on the total area of the first surface of the adhesive layer. Preferably, the first further layer has at least one first layer surface and a further layer surface. The first and/or further layer surface of the first further layer preferably has an area within a range from 1 mm² to 1000 m², or preferably within a range from 100 mm² to 500 m², or preferably within a range from 1 cm² to 100 m². Preferably, the first and/or further layer surface of the first further layer has a total surface area greater than the total surface area of the first surface of the adhesive layer. Preferably, the first and/or further layer surface of the first further layer has a total surface area within a range from 105% to 200%, or preferably within a range from 110% to 190%, or preferably within a range from 120% to 180%, based on the total surface area of the first surface of the adhesive layer. In a further preferred execution, the first and/or further layer surface of the first further layer has a total surface area not less than the total surface area of the first surface of the adhesive layer.

Preferably, the first layer surface of the first further layer is in direct contact with the first surface of the adhesive layer. Alternatively, an additional material, such as a primer, for example based on alkyd resin or acrylic resin, may be at least partly disposed between the first further layer and the adhesive layer. The first further layer, before being contacted by the adhesive layer, is preferably pretreated by means of a surface treatment method selected from the group consisting of plasma treatment, ozone treatment and corona treatment, or a combination of at least two of these.

The at least one first further layer preferably includes a material selected from the group consisting of a polymer, a nonwoven, a weave, a glass, a metal, a ceramic, a mineral, a paper or a combination or mixture of at least two of these.

The polymer may be any polymer that the person skilled in the art would select for the first further layer. The polymer is preferably selected from the group consisting of a polyvinyl chloride, a polyolefin, such as polyethylene or polypropylene, a polyimide, a polyethylene terephthalate, a polybutylene terephthalate, a polycarbonate, a polyamide, a polyurethane, such as a thermoplastic polyurethane, a silicone or a mixture or combination of at least two of these. More preferably, the polymer is selected from the group consisting of a polyester, a polyolefin, a polyvinyl chloride, a silicone, a thermoplastic polyurethane, and among these more preferably a thermoplastic polyurethane.

The nonwoven may be any nonwoven that the person skilled in the art would select for the first further layer. The nonwoven is preferably selected from the group consisting of plant fibers, such as cotton, animal fibers, such as wool, synthetic fibers made from natural polymers, such as viscose, synthetic fibers made from synthetic polymers, such as polyester nonwovens, and synthetic fibers made from mineral substances, such as glass fiber nonwoven, carbon fiber nonwoven, stainless steel fiber nonwoven, basalt fiber nonwoven, or a mixture of at least two of these.

The weave may be any weave that the person skilled in the art would select for the first further layer. The weave is preferably selected from the group consisting of a cotton weave, a wool weave or a combination of at least two of these.

The glass may be any glass that the person skilled in the art would select for the first further layer. The glass may be a metallic glass or a nonmetallic glass. The glass is preferably a nonmetallic glass. The glass is preferably selected from the group consisting of a silicate glass, such as quartz glass, a borate glass, a phosphatic glass, a chalcogenide glass, a halide glass or a mixture of at least two of these.

The metal may be any metal that the person skilled in the art would select for the first further layer. The metal is preferably selected from the group consisting of copper, iron, silver, gold, platinum, palladium, nickel, a bronze alloy, a brass alloy or a mixture or combination of at least two of these.

The ceramic may be any ceramic that the person skilled in the art would select for the first further layer. The ceramic is preferably an oxide ceramic or a non-oxide ceramic. The oxide ceramic is preferably selected from the group consisting of an aluminum oxide ceramic, such as corundum, a beryllium oxide ceramic, a zirconium(IV) oxide ceramic, a titanium(IV) oxide ceramic, an aluminum-titanium ceramic, a barium titanate ceramic or a mixture or combination of at least two of these. The non-oxide ceramic is preferably selected from the group consisting of a silicon carbide, a boron nitride, a boron carbide, a silicon nitride, an aluminum nitride, a molybdenum silicide, a tungsten carbide or a mixture or combination of at least two of these.

The mineral may be any mineral that the person skilled in the art would select for the first further layer. According to the invention, a mineral is understood to mean any element or any chemical compound that has been formed in a generally crystalline manner and by geological processes. The term "chemical compound" includes a fixed composition and a defined chemical structure. Mixtures of matter are not minerals. However, the compositions of minerals can have a certain variation (mixed crystals), provided that they are structurally homogeneous.

The mineral may have been formed from organic constituents or from inorganic constituents or from a combination of the two. The organic constituents are preferably selected from the group consisting of mellite, evenkite, whewellite, weddellite or a mixture of at least two of these. The inorganic constituents are preferably selected from the group consisting of borax, amber, potash feldspar, feldspar, calcite, kaolinite or a combination of at least two of these.

The paper may be any paper that the person skilled in the art would select for the first further layer. The paper is preferably selected from the group consisting of a natural paper and a synthetic paper or a combination of these. The natural paper includes cellulose as a main constituent. The synthetic paper may additionally include a polymer. The polymer is preferably selected from the group of the polymers as described above. The paper preferably has a mass per unit area within a range from 20 to 500 $g/m^2$, or preferably within a range from 20 to 400 $g/m^2$, or preferably within a range from 20 to 200 $g/m^2$, or preferably within a range from 50 to 500 $g/m^2$, or preferably within a range from 100 to 500 $g/m^2$, or preferably within a range from 200 to 500 $g/m^2$.

The paper preferably has a coating. The coating preferably includes a polymer selected from the group as already described above. The polymer preferably covers the paper to an extent of at least 50%, or preferably to an extent of at least 60%, or to an extent of at least 80%, based on the total surface area of the paper. More preferably, the polymer covers the paper over its entire surface area. The polymer is preferably a silicone or a polyolefin that forms a wax on the paper. The parameters for coating of the paper by a silicone wax or polyolefin wax are preferably chosen such that the adhesive layer is detachable from the paper in a residue-free manner.

The surface roughness of the first further layer, especially of the paper layer, is within a region of Rz<2000 nm, preferably <1500 nm, or preferably <1000 nm. Surface roughness is ascertained by means of white light interferometry (measurement in PSI mode) in accordance with DIN EN ISO 25178, Part 6.

In a preferred configuration of the adhesive layer, the adhesive layer is at least partly covered on its first further surface at least by a second further layer. The second further layer may be manufactured from any material that the person skilled in the art would select for the second further layer. The second further layer preferably has the same constituents, materials, properties, shapes and dimensions as described for the first further layer.

Preferably, the first further layer and/or the second further layer are in direct contact with the first layer. Alternatively, a third further layer may be disposed between the first further layer and/or the second further layer and the first layer. The properties, materials, shapes and dimensions of the third further layer are preferably selected from the list as described for the first further layer.

Preferably, the first further layer and/or the second further layer art readily detachable from the adhesive layer. According to the invention, "readily detachable" is understood to mean that a user of the adhesive layer can undertake the detachment of the first further layer and/or the second further layer without perceptible expenditure of force. Preferably, the force expended to detach the first further layer and/or the second further layer is within a range from 0.02 to 2 N/10 mm, preferably 0.05 to 1 N/10 mm.

The first further layer and/or second further layer are preferably configured such that they protect the adhesive layer from external influences, such as dust, liquids, moisture, temperature, pressure and other influences. The first further layer and/or second further layer are preferably overlaid over the adhesive layer for the purposes of transport of the adhesive layer. The first further layer and/or second further layer serve in particular for easy transfer of the adhesive layer to the surface of a product.

Preference is given to a product, wherein the product includes an adhesive as described above and further has at least one of the following features:
at least one substrate,
at least one component including at least one component surface.

It is further preferable that the product has at least one, preferably two, or preferably all, of the following features:
at least one first layer,
at least one first further layer,
at least one second further layer.

The product may be any product that the person skilled in the art would select which can have an adhesive layer. The product is preferably selected from the group consisting of a medical product, a domestic product, a means of transport, a means of communication, or a combination of at least two of these.

The medical product may be any product that the person skilled in the art would use for medical purposes. According to the invention, a medical product is understood to mean any product used on the patient by medical personnel, such as doctors, nurses, doctor's assistants etc., or used by the patient on him-/herself or on another person for monitoring of a parameter, for treatment of a disease or wound or for improvement of his/her state of health. The medical product is preferably selected from the group consisting of a medical device, a medical article or a combination of these. By contrast with a medical article, the medical device has a power supply or at least one fitting for connection to a power supply.

The medical device may be any device that the person skilled in the art would select for examination or treatment of a patient. The medical device is preferably selected from the group consisting of a diagnostic device, a therapeutic device, a surgical device or a combination of at least two of these. Examples of diagnostic devices are a thermometer, a blood pressure gauge, a pulse meter, a blood sugar meter and the elements that secure them to the user's body. Examples of therapeutic devices are a device for negative pressure wound therapy, a pacemaker, an insulin pump, a defibrillator, for example an implantable defibrillator, or a combination of at least two of these. Examples of a surgical device are dental treatment instruments such as a dentist's drill, electrical scalpel or combination of at least two of these.

The medical article may be any article that the person skilled in the art would select for treatment of a patient. The medical article is preferably selected from the group consisting of a catheter, a container for an ostomy, a medical tape, a scalpel, a syringe, a cannula, a means of wound treatment, such as a plaster, a medical bandage, a reusable cloth, a disposable cloth or a combination of at least two of these. The characteristic property of the medical bandage, the reusable cloth, the disposable cloth is their ability to absorb liquids, especially blood, as can occur in the event of diagnostic, therapeutic or surgical interventions. The distinction between bandage and cloth is made on the basis of their material composition. Bandage may contain, for example, both natural materials, such as cotton and/or wool, in combination with synthetic materials, while cloth consists purely of cotton.

Preferably, the product is selected from the group consisting of a container for an ostomy, a means of wound treatment, a medical tape, a device for negative pressure wound therapy and a wearable device, i.e. a portable electronic medical device, e.g. a blood pressure meter or another sensor that is stuck to the user's skin for monitoring, or a combination of at least two of these.

The domestic product may be any domestic product that the person skilled in the art would select for this purpose. The domestic product is preferably selected from the group consisting of a mixer, a stirrer system, a cutting machine, a serving plate or a combination of at least two of these.

The means of transport may be any means of transport that the person skilled in the art would select for this purpose. The means of transport is preferably selected from the group consisting of a car, an aircraft, a motorcycle, a bicycle, a moped, an inline skate or a combination of at least two of these.

The means of communication may be any means of communication that the person skilled in the art would select for this purpose, especially a device that serves to transfer data. The means of communication is preferably selected from the group consisting of a telephone, a mobile phone, a fax device, a modem, a computer, a GPS device, a navigation device or a combination of at least two of these.

The product may include the adhesive for various purposes. The product includes the adhesive preferably for bonding of product parts to one another. In an additional or alternative configuration of the product, the product includes the adhesive in order to secure the product to a further product, to a further article, or to the skin of a user of the product. The article may be any article that the person skilled in the art would connect to the product. The adhesive that the product includes preferably serves to secure the product to the skin of a user.

The substrate may be any substrate that the person skilled in the art would select for a product of the invention. The substrate preferably includes a material selected from the group consisting of a polymer, a metal, a weave, a nonwoven, a mineral or a combination of at least two of these. The substrate material, such as the polymer, the metal, the weave, the nonwoven, the mineral or combinations thereof, is preferably selected from the group of materials as described for the first further layer. The substrate may have any shape that the person skilled in the art would select for the substrate. Preferably, the substrate has a two-dimensional shape. Preferably, the substrate has a thickness within a range from 10 µm to 10 cm, or preferably within a range from 100 µm to 10 cm, or preferably within a range from 1 mm to 10 cm, or preferably within a range from 10 µm to 1 cm, or preferably within a range from 10 µm to 1 mm, or preferably within a range from 1 mm to 1 cm. The substrate preferably has a flexible structure. The substrate is preferably sufficiently flexible that it can fit the contours of a human body.

The substrate is preferably selected from the group consisting of a film, including a thermoplastic PU film, a release paper, a nonwoven (for example for adhesive tapes), a PU foam or a combination of at least two of these.

The component may be any component that the person skilled in the art would select for a product of the invention. The component is preferably selected from the group consisting of a device component of the device that has been described above in connection with the product. The material of which the component consists, especially the at least one component surface, is preferably selected from the group consisting of the materials as already described for the first further layer.

The component may constitute part of the product or the entire product. The adhesive preferably serves to bond various components of the product to one another to form the product. Alternatively or additionally, the adhesive may serve to bond the component to the skin of a user of the product. Further alternatively or additionally, the adhesive may serve to bond the product to a further article. The article may be any article that the person skilled in the art would connect to the product.

The component includes at least one component surface. At least part of the component surface preferably serves to come into contact with the adhesive or to be covered by the adhesive. The adhesive present at the component surface can bond the component to other articles or to the skin of a user.

The adhesive present in the product is preferably applied in the form of dots or over part or all of the area of the substrate or at least one component surface of a component. Preferably, the adhesive is applied to the substrate or component, for example in the form of a particular pattern, for example a repeating or replicative pattern, especially to at least part of a component surface. Preferably, the adhesive is applied in the form of a layer to the substrate or at least one component surface of a component. Preferably, the adhesive present in the product is bonded to the product in the form of the first layer as described in connection with the adhesive layer. Preferably, the adhesive layer is bonded directly to the substrate or the component.

Before, during or after the bonding of the substrate or the component to the adhesive layer, the adhesive layer may have at least one first further layer or one second further layer on one of its surfaces. If the adhesive layer, prior to the bonding to the substrate or the component, has one further layer each on at least two surfaces, at least one of the further layers is removed prior to contact with the substrate or the component. The other further layer, for example the second further layer, can remain on the adhesive layer for protection thereof until the substrate or component is bonded to a further article or the skin of a patient. The first layer, the first further layer and the second further layer are preferably each constructed and configured in the same way, as already described above in connection with the adhesive layer.

In a preferred configuration of the product, the product is selected from the group consisting of a plaster, a (wound) dressing, a tape, a self-adhesive tape, a stoma pouch for an ostomy, a blood-absorbing bandage, a bandage, a medical device or at least one constituent of these end products.

The invention further provides a kit having components (V1) and (V2). The constituents, the ratios thereof and the process for producing components (V1) and (V2) correspond to those of components A) to L) described in connection with the adhesive of the invention. Components (V1) and (V2) are preferably processed in accordance with the process of the invention for producing a layer construction including at least one adhesive layer.

EXAMPLES

The invention is illustrated in detail by the examples which follow, but without being restricted thereto.

Methods:

Unless indicated otherwise, all percentages are based on weight and the total amount or on the total weight of the compositions.

Unless stated otherwise, all analytical measurements relate to measurements at temperatures of 23° C.

Solids contents were ascertained in accordance with DIN EN 3251 by heating a weighed sample to 105° C. to constant weight. At constant weight, the solids content was calculated by reweighing the sample.

Unless explicitly mentioned otherwise, NCO values were determined by volumetric means to DIN-EN ISO 11909.

The check for free NCO groups was conducted by means of IR spectroscopy (band at 2260 $cm^{-1}$).

The viscosities reported were determined by means of rotary viscometry to DIN 53019 at 23° C. with a rotary viscometer from Anton Paar Germany GmbH, Ostfildern, DE (1 Pa s=1 N/m$^2$*s).

Average particle sizes (the number-average is specified) of the polyurethane dispersions were determined after dilution with deionized water by means of laser correlation spectroscopy (instrument: Malvern Zetasizer 1000, Malvern Inst. Limited).

The pH was measured by the method described in DIN ISO 976 on the undiluted sample.

Glass transition temperature $T_g$ was determined by dynamic differential calorimetry (DSC) in accordance with DIN EN 61006, Method A, using a DSC instrument (Perkin-Elmer Pyris Diamond DSC calorimeter) that was calibrated with indium and lead for determination of $T_g$. 10 mg of the substance to be analyzed were weighed into a sealable aluminum crucible, which was sealed. Three successive runs of a heating operation from −100° C. to +150° C., heating rate 20 K/min, with subsequent cooling at cooling rate 320 K/min were undertaken, and the third heating curve was used to determine the values. $T_g$ is the temperature determined at half the height of a glass transition step.

Determination of Peel Force (90° Peel Test) to DIN EN 1464

The peel force was determined with a tensile tester according to DIN EN ISO 527-1 and a roller peel device. The adhesive layer to be examined was reinforced on its reverse side with an adhesive tape (TESA4104) and cut to size of 20×2 cm$^2$. The release paper side of the adhesive layer is stuck to an acetone-clean aluminum sheet (from Krüppel, Krefeld; 99.9% ultrapure aluminum) (20×2 cm$^2$) with 3 twin strokes of a 4 kg roller. After a contact time of 60 min with the aluminum substrate, the peel force is determined to DIN 1464 at a peel angle of 90° with separation of the joined parts. The peeling rate is 300 mm/min. The peeling force is reported in N/20 mm.

Determination of Moisture Vapor Transmission Rate, Also MVTR

MVTR is determined in accordance with DIN EN13726-2 (Part 3.2). This involves filling a metal cylinder with water as described in the DIN standard and closing it at the top end with the film to be examined or the layer to be examined. Subsequently, the total weight (beaker with water and film) is determined by means of a balance. The measurement setup is stored at 37° C. for 24 h and the weight is determined again. The loss of water that evaporates through the film is ascertained by subtraction. MVTR is reported in g/(m$^2$*24 h).

Substances and Abbreviations Used

Diaminosulfonate: NH$_2$—CH$_2$CH$_2$—NH—CH$_2$CH$_2$—SO$_3$Na (45% in water)

PolyTHF 1000 poly(tetramethylene glycol) polyetherdiol having number-average molar mass 1000 g/mol, BASF SE, Ludwigshafen, DE PolyTHF 2000 poly(tetramethylene glycol) polyetherdiol having number-average molar mass 2000 g/mol, BASF SE, Ludwigshafen, DE PPG polypropylene glycol, Covestro AG, Leverkusen, DE. Unless stated otherwise, PPG was prepared via KOH catalysis.

Desmodur N 3300 aliphatic polyisocyanate (HDI isocyanurate), NCO content about 21.8%, Covestro AG, Leverkusen, Germany Water water demineralized by ion exchanger Baymedix® FP520 Hydrophilic, aliphatic polyisocyanate based on hexamethylene diisocyanate (HDI), Covestro AG, Leverkusen, Germany The isocyanate components used are commercial products from Covestro Deutschland AG, Leverkusen, DE. Further chemicals were purchased from Sigma-Aldrich Chemie GmbH, Taufkirchen, DE. Unless stated otherwise, the raw materials were used without further purification or pretreatment.

Amorphous Polgurethaneurea Dispersion 1 (V1)

60.0 g of polypropylene glycol having a number-average molar mass of 1000 g/mol and 280 g of polypropylene glycol having a number-average molar mass of 2000 g/mol were heated up to 65° C. Subsequently, a mixture of 30.1 g of hexamethylene diisocyanate and 39.8 g of isophorone diisocyanate and 2 drops of tin octanoate was added, and the mixture was stirred at 130° C. until the NCO value had gone below the theoretical value (about 90 min). The finished prepolymer was dissolved with 730 g of acetone at 50° C. and then a solution of 3.0 g of ethylenediamine, 18.9 g of diaminosulfonate, 3.6 g of diethanolamine and 74 g of water was metered in at 40° C. The mixture was stirred for a further 15 min. This was followed by dispersion by addition of 550 g of water. Subsequently, the solvent was removed by distillation under reduced pressure, and a storage-stable dispersion was obtained; the solids content was adjusted by addition of water.

Solids content: 41%

Particle size (LCS): 160 nm

Viscosity: 365 mPa s

Use Example 1 (Comparative Example)

100 g of the (inventive) polyurethane dispersion 1 were initially charged together with 2 g of a 10% by weight aqueous Rheolate 208 dispersion in a Speedmixer cup. Bubble-free mixing to give a polyurethaneurea composition is effected in the Speedmixer at a speed of 2750 min' for 1 minute. After application by means of an Erichsen drawdown bar (200 μm) to a release paper from Felix Schöller with the Y5900 name, drying was effected at 40° C. for 20 minutes and at 130° C. for 10 min. MVTR: 1950 g/d m$^2$.

Peel force measurement: cohesion fracture even with small expenditure of force

Use Example 2 (Inventive)

Production of a film from the polyurethaneurea dispersion 1 was as in use example 1, except that, after the introduction of the Rheolate, 1.9% by weight of Baymedix® FP520 was additionally mixed in by means of a Speedmixer at 2750 min$^{-1}$ for 1 min.

Peel force measurement: 8.8 N/20 mm

Use Example 3 (Inventive)

Production of a film from the polyurethaneurea dispersion 1 was as in use example 2, except with an addition of 3.8% by weight of Baymedix® FP520.

Peel force measurement: 5.8 N/20 mm

Use Example 4 (Inventive)

Production of a film from the polyurethaneurea dispersion 1 was as in use example 2, except with an addition of 6.8% by weight of Baymedix® FP520.
Peel force measurement: 1.5 N/20 mm As apparent from the examples, the peel force of the adhesive layers produced from the adhesive of the invention can be adjusted in a controlled manner by choice of the amount of added component (V2) in the form of Baymedix® FP520 as polyisocyanate. Higher amounts (V2) lead to lower peel force. Thus, it is possible to tailor the bonding force of component (V1) which is too high for sensitive applications such as bonding to skin or wounds for each application without any need, as in the prior art, for a complicated processing method with additional steps. The adhesive systems used in the prior art that enable an adjustable bonding force are two-component reactive systems. Once mixed, these have only a very limited processing time since polymerization or crosslinking sets in directly after mixing and hence there is a continuous change in the flow and coating characteristics of the mixture. In this respect, these can be produced only by an inline mixing technique and with elevated cleaning complexity of the application system, associated with process interruptions.

The invention claimed is:

1. An adhesive producible from an aqueous polyurethaneurea dispersion comprising
 (V1) a polyurethaneurea obtained by reacting a polyurethaneurea reaction mixture comprising
 A) an aliphatic, cycloaliphatic or araliphatic polyisocyanate component having an average isocyanate functionality of ≥1.8 and ≤2.6,
 B) a polymeric polyetherpolyol component,
 C) an amino-functional chain extender component having at least 2 isocyanate-reactive amino groups, comprising an amino-functional compound C1) that does not have any ionic or ionogenic groups and/or an amino-functional compound C2) that has ionic or ionogenic groups,
 D) optionally a further hydrophilizing components different than C2),
 E) optionally a hydroxy-functional compounds having a molecular weight of 62 to 399 mol/g,
 F) optionally a further polymeric polyols different than B),
 G) optionally a compound having exactly one isocyanate-reactive group or a compound having more than one isocyanate-reactive group, where only one of the isocyanate-reactive groups reacts with isocyanate groups present in the polyurethaneurea reaction mixture, and
 H) optionally one aliphatic, cycloaliphatic or araliphatic polyisocyanate component having an average isocyanate functionality of >2.6 and ≤4,
 wherein component F) is present in an amount of 30% by weight, based on a total mass of components B) and F); and
 (V2) a hydrophilic polyisocyanate prepared from at least components
 I) an aliphatic, cycloaliphatic or araliphatic polyisocyanate component having an average isocyanate functionality of ≥2.0 and ≤3.6,
 J) a polymeric, hydrophilic and monofunctional polyalkylene oxide component,
 K) optionally a further hydrophilizing components different than J),
 L) optionally an admixture, an auxiliary, or a combination thereof.

2. The adhesive as claimed in claim 1, wherein component A) is isophorone diisocyanate, hexamethylene diisocyanate or a mixture of isophorone diisocyanate and hexamethylene diisocyanate.

3. The adhesive as claimed in claim 1, wherein component B) comprises a poly(propylene glycol) polyetherpolyols.

4. The adhesive as claimed in claim 1, wherein component B) has an average molar mass within a range from 400 to 4000 g/mol.

5. The adhesive as claimed in claim 1, wherein component B) comprises a mixture of poly(propylene glycol) polyetherpolyols, wherein individual poly(propylene glycol) polyetherpolyols of the mixture differ in number-average molecular weight by at least 100 g/mol.

6. The adhesive as claimed in claim 1, wherein component C) comprises an amino-functional compound C1) having no ionic or ionogenic groups and an amino-functional compound C2) having ionic or ionogenic groups.

7. The adhesive as claimed in claim 1, wherein component D) comprises a nonionically hydrophilizing components D1).

8. The adhesive as claimed in claim 1, wherein the polyurethaneurea is obtained by preparing an isocyanate-functional polyurethane prepolymers a) from components A), B) and optionally D) and/or C2), and optionally compounds E) and/or H), wherein free NCO groups thereof are then wholly or partially reacted with the amino-functional chain-extender component C), and also component G) and optionally component D).

9. The adhesive as claimed in claim 1, wherein the polyurethaneurea has a Tg≤−25° C.

10. The adhesive as claimed in claim 1, wherein
 I) comprises at least one of
  I1.) a low molecular weight aliphatic, cycloaliphatic or araliphatic diisocyanates of molar mass from 140 two 278 g/mol;
  I2.) a polyisocyanates preparable from I1.) and having an isocyanate functionality of 2 to 3.6; or
  I3. a combination of I1.) and I2.);
 J) comprises at least one of
  J1.) a monofunctional polyalkylene oxide of OH number from 10 to 250;
  J2.)ethylene oxide, propylene oxide, butylene oxide, pentylene oxide or a mixture of at least two of these;
  J3.) a monofunctional polyalkylene oxide having an ethylene oxide content of 50 to 100 mol % based on total amount of oxyalkylene groups present; or
  J4.) a combination of at least two of J1.) to J3.).

11. An aqueous polyurethaneurea dispersion comprising
 (V1) an amorphous polyurethaneurea obtained by reacting a polyurethaneurea reaction mixture comprising
 A) an aliphatic, cycloaliphatic or araliphatic polyisocyanate component having an average isocyanate functionality of ≥1.8 and ≤2.6,
 B) a polymeric polyetherpolyol component,
 C) an amino-functional chain extender component having at least 2 isocyanate-reactive amino groups, comprising an amino-functional compound C1) that does not have any ionic or ionogenic groups and/or an amino-functional compound C2) that has ionic or ionogenic groups,
 D) optionally a further hydrophilizing components different than C2),
 E) optionally a hydroxy-functional compounds having a molecular weight of 62 to 399 mol/g, F) optionally a further polymeric polyol different than B), G) optionally a compound having exactly one isocyanate-reactive group that reacts with isocyanate groups present in the polyurethaneurea reaction mixture, and H) optionally an aliphatic, cycloaliphatic or araliphatic polyisocyanate component having an average isocyanate functionality of ≥2.6 and ≤4, wherein F) is present in an amount of ≤30% by weight, based on a total mass of components B) and F); and (V2) a hydrophilic polyisocyanate prepared from at least components I) an aliphatic, cycloaliphatic or araliphatic polyisocyanate component having an average isocyanate functionality of ≥2.0 and ≤3.6, J) a polymeric, hydrophilic and monofunctional polyalkylene oxide component, K) optionally a further hydrophilizing components different than J), L) optionally an admixture, an auxiliary, or a combination thereof.

12. A process for producing a layer construction including an adhesive layer, comprising:

(I) mixing a hydrophilic polyisocyanate (V2) into a polyurethaneurea (V1) to obtain a polyurethaneurea dispersion as claimed in claim 11, (II) applying the polyurethaneurea dispersion from step (I) to a first further layer to obtain a precursor, (III) thermally treating the precursor at a temperatures within a range from 20° C. to 200° C. to form the adhesive layer.

13. The process as claimed in claim 12, further comprising at least one of the following:

(IV) detaching the adhesive layer from the first further layer;

(V) transferring the adhesive layer from the first further layer to a second further layer;

(VI) covering the adhesive layer with the second further layer on tea first surface of the first further layer;

(VII) covering the adhesive layer with the second further layer on tea first further surface of the first further layer;

(VIII) transferring the adhesive layer from the first further layer to a substrate;

(IX) transferring the adhesive layer from the first further layer to at least a portion of a component surface of a component;

(X) transferring the adhesive layer from the first further layer to a third further layer.

14. A method of securing a product on an article or on skin of a living being, comprising: adhering the product to the article or skin using the adhesive of claim 1.

15. A kit, comprising:

(V1) an amorphous polyurethaneurea obtained by reacting a polyurethaneurea reaction mixture comprising A) an aliphatic, cycloaliphatic or araliphatic polyisocyanate component having an average isocyanate functionality of ≥1.8 and ≤2.6, B) a polymeric polyetherpolyol component, C) an amino-functional chain extender component having at least 2 isocyanate-reactive amino groups, comprising an amino-functional compound C1) that does not have any ionic or ionogenic groups and/or an amino-functional compound C2) that has ionic or ionogenic groups, D) optionally a further hydrophilizing components different than C2), E) optionally a hydroxy-functional compounds having a molecular weight of 62 to 399 mol/g, F) optionally a further polymeric polyol different than B), G) optionally a compound having exactly one isocyanate-reactive group or one compound having more than one isocyanate-reactive group, where only one of the isocyanate-reactive groups reacts with isocyanate groups present in the polyurethaneurea reaction mixture, and H) optionally an aliphatic, cycloaliphatic or araliphatic polyisocyanate component having an average isocyanate functionality of >2.6 and ≤4, wherein component F) is present in an amount of ≤30% by weight, based on a total mass of components B) and F); and (V2) a hydrophilic polyisocyanate prepared from at least components I) an aliphatic, cycloaliphatic or araliphatic polyisocyanate component having an average isocyanate functionality of ≥2.0 and ≤3.6, J) a polymeric, hydrophilic and monofunctional polyalkylene oxide component, K) optionally a further hydrophilizing components different than J), and L) optionally an admixture, an auxiliary, or a combination thereof.

* * * * *